US012649736B2

(12) United States Patent
Jung et al.

(10) Patent No.: US 12,649,736 B2
(45) Date of Patent: Jun. 9, 2026

(54) SYNTHESIS OF COMPOUNDS TO PROMOTE HAIR GROWTH

(71) Applicant: The Regents of the University of California, Oakland, CA (US)

(72) Inventors: Michael E. Jung, Los Angeles, CA (US); Xiaoguang Liu, Santa Monica, CA (US)

(73) Assignee: The Regents of the University of California, Oakland, CA (US)

(*) Notice: Subject to any disclaimer, the term of this patent is extended or adjusted under 35 U.S.C. 154(b) by 849 days.

(21) Appl. No.: 17/786,986

(22) PCT Filed: Dec. 18, 2020

(86) PCT No.: PCT/US2020/066078

§ 371 (c)(1),
(2) Date: Jun. 17, 2022

(87) PCT Pub. No.: WO2021/127482

PCT Pub. Date: Jun. 24, 2021

(65) Prior Publication Data

US 2023/0103693 A1 Apr. 6, 2023

Related U.S. Application Data

(60) Provisional application No. 62/951,667, filed on Dec. 20, 2019.

(51) Int. Cl.
*C07D 471/04* (2006.01)

(52) U.S. Cl.
CPC .................................. *C07D 471/04* (2013.01)

(58) Field of Classification Search
CPC .. C07D 209/10; C07D 209/12; C07D 209/14; C07D 209/18; C07D 213/46; C07D 213/54; C07D 213/76; C07D 213/81; C07D 471/04
See application file for complete search history.

(56) References Cited

U.S. PATENT DOCUMENTS

| | | | |
|---|---|---|---|
| 3,524,860 A | 8/1970 | Albertson | |
| 5,124,354 A | 6/1992 | Green | |
| 5,397,787 A | 3/1995 | Buzzetti et al. | |
| 5,663,346 A | 9/1997 | Buzzetti et al. | |
| 6,541,507 B1 | 4/2003 | Dalko et al. | |
| 8,470,849 B2 * | 6/2013 | Carniato .................. | A61P 3/10 546/113 |
| 9,499,551 B2 | 11/2016 | Jacobsen et al. | |
| 11,213,513 B2 | 1/2022 | Lowry et al. | |
| 11,312,714 B2 | 4/2022 | Lowry et al. | |
| 11,472,804 B2 | 10/2022 | Lowry et al. | |
| 11,787,804 B2 | 10/2023 | Lowry et al. | |
| 12,227,503 B2 | 2/2025 | Lowry et al. | |
| 2008/0064765 A1 | 3/2008 | Birnbaum | |
| 2009/0269418 A1 | 10/2009 | Albeck et al. | |
| 2010/0305187 A1 | 12/2010 | Guelow et al. | |
| 2011/0028460 A1 | 2/2011 | Kisak et al. | |
| 2013/0023587 A1 | 1/2013 | Schroeder et al. | |
| 2013/0337031 A1 | 12/2013 | Kisak et al. | |
| 2015/0140071 A1 | 5/2015 | Rajasekaran | |
| 2020/0030289 A1 | 1/2020 | Lowry et al. | |
| 2020/0157093 A1 | 5/2020 | Lowry et al. | |
| 2020/0253917 A1 | 8/2020 | Lowry et al. | |
| 2022/0048908 A1 | 2/2022 | Lowry et al. | |
| 2022/0153738 A1 | 5/2022 | Lowry et al. | |
| 2023/0103693 A1 | 4/2023 | Jung et al. | |
| 2023/0114220 A1 | 4/2023 | Lowry et al. | |
| 2023/0322765 A1 | 10/2023 | Sun et al. | |
| 2024/0025895 A1 | 1/2024 | Lowry et al. | |
| 2024/0327400 A1 | 10/2024 | Sun et al. | |
| 2025/0145626 A1 | 5/2025 | Sun et al. | |
| 2025/0163045 A1 | 5/2025 | Sun et al. | |
| 2025/0304579 A1 | 10/2025 | Lowry et al. | |

FOREIGN PATENT DOCUMENTS

| | | | |
|---|---|---|---|
| CN | 1093707 | A | 10/1994 |
| CN | 106880693 | A | 6/2017 |
| DE | 3601285 | A1 | 7/1987 |
| EP | 0403238 | A2 | 12/1990 |
| EP | 0780389 | A1 | 6/1997 |
| EP | 1068858 | A1 | 1/2001 |
| JP | S 59-161357 | A | 9/1984 |
| WO | WO-9200057 | A1 | 1/1992 |
| WO | WO-1992/007839 | A1 | 5/1992 |
| WO | WO-96/00226 | A1 | 1/1996 |
| WO | WO-0162237 | A2 | 8/2001 |
| WO | WO-03/007951 | A1 | 1/2003 |
| WO | WO-2004/080481 | A1 | 9/2004 |
| WO | WO-2005/051908 | A1 | 6/2005 |
| WO | WO-2005/054247 | A1 | 6/2005 |
| WO | WO-2005/123664 | A2 | 12/2005 |
| WO | WO-2005/123731 | A2 | 12/2005 |

(Continued)

OTHER PUBLICATIONS

Valeur et al., Bioorganic & Medicinal Chemistry Letters, 22, 2012, pp. 5909-5914. (Year: 2012).*
Khan et al., Chemical and Pharmaceutical Bulletin, Nov. 25, 1977, 25(11), pp. 3110-3114. (Year: 1977).*
CAS Registry No. 139336-32-6: Entered STN: Feb. 28, 1992.
CAS Registry No. 861644-67-9: Entered STN: Aug. 8, 2005.
CAS Registry No. 96618-51-8: Entered STN: Jan. 3, 1985.
Fairhurst et al., "A synthesis of CIS-α, β-unsaturated nitriles by kinetically controlled decarboxylation" Tetrahedron Letters, No. 22, pp. 3843-3844 (1975).
Harisha et al., "Reaction of 3-arylidenepropenoic acid derivatives with triethylamine and other amines; unexpected reductions and vinylogations" Tetrahedron Letters, No. 72, pp. 2880-2889 (2016).

(Continued)

*Primary Examiner* — Laura L Stockton
(74) *Attorney, Agent, or Firm* — Foley Hoag LLP; David P. Halstead; Alexander J. Chatterly

(57) ABSTRACT

The present disclosure relates to a method of synthesizing a compound represented by formula I.

6 Claims, No Drawings

(56) References Cited

FOREIGN PATENT DOCUMENTS

| | | | |
|---|---|---|---|
| WO | WO-2007/002433 | A1 | 1/2007 |
| WO | WO-2007/062998 | A1 | 6/2007 |
| WO | WO-2007/068418 | A1 | 6/2007 |
| WO | WO-2007/099396 | A2 | 9/2007 |
| WO | WO-2008/028118 | A1 | 3/2008 |
| WO | WO-2009/059666 | A1 | 5/2009 |
| WO | WO-2010/001169 | A2 | 1/2010 |
| WO | WO-2012/078649 | A1 | 6/2012 |
| WO | WO-2013/128465 | A1 | 9/2013 |
| WO | WO-2013/169956 | A2 | 11/2013 |
| WO | WO-2013/188554 | A1 | 12/2013 |
| WO | WO-2014/113467 | A1 | 7/2014 |
| WO | WO-2014/207213 | A1 | 12/2014 |
| WO | WO-2015/042053 | A1 | 3/2015 |
| WO | WO-2015/049365 | A2 | 4/2015 |
| WO | WO-2015/112854 | A1 | 7/2015 |
| WO | WO-2017/196936 | A1 | 11/2017 |
| WO | WO-2018/039612 | A1 | 3/2018 |
| WO | WO-2018/039615 | A1 | 3/2018 |
| WO | WO-2019/006359 | A1 | 1/2019 |
| WO | WO-2020/142413 | A1 | 7/2020 |
| WO | WO-2021/127482 | A1 | 6/2021 |
| WO | WO-2022/006039 | A1 | 1/2022 |
| WO | WO-2022/006040 | A1 | 1/2022 |
| WO | WO-2021/127482 | A8 | 6/2022 |

OTHER PUBLICATIONS

Salin et al., "Phosphine-catalyzed addition of P(O)—H compounds to ethyl phenylpropiolate" Tetrahedron Letters, No. 56, pp. 6282-6286 (2015).
Shelke et al., "An Efficient Synthesis of 5-Arylidene-2,4-ThiazolidinedioneCatalyzed by Boric acid in Aqueous media under Ultrasound-Irradiation" Chemistry and Biology Interface, vol. 6, No. 6, pp. 410-415 (2016).
Date et al., "A Highly Regio- and Stereoselective Vinylogous Horner-Wadsworth-Emmons Route to Densely Substituted 1, 3?Butadienes", Angewandte Chemie International Edition 46.3: 386-388 (2007).
Extended European Search Report for EP Application No. 20903755.5 dated Jan. 9, 2024.
Gordon et al., "Development of Second-Generation Indole-Based Dynamin GTPase Inhibitors" Journal of Medicinal Chemistry, vol. 56, p. 46-59 (2013).
Krawyczyk et al., "Knoevenagel Reaction of Diethylphosphonoacetic Acid: A Facile Route to Diethyl (E)-2-Arylvinylphosphonates" Synthesis, No. 17, p. 2887-2896 (2005).
Moriya et al., "Preparation and reactions of 3-(aminomethylene)-3H-indoles", Chemical and Pharmaceutical Bulletin 28.6: 1711-1721 (1980).
Silverman et al., "The Organic Chemistry of Drug Design and Drug Action" translated bu Guo Zongru, Chemical Industry Press, 1st edition, pp. 17-23, Jan. 31, 2008.
STN Registry Database, RN 302562-57-8, entered Nov. 13, 2000.
STN Registry Database, RN 302562-58-9, entered Nov. 13, 2000.
STN Registry Database, RN 302825-78-1, entered Nov. 14, 2000.
STN Registry Database, RN 303202-38-2, entered Nov. 20, 2000.
STN Registry Database, RN 327076-80-2, entered Mar. 14, 2001.
STN Registry Database, RN 327076-81-3, entered Mar. 14, 2001.
STN Registry Database, RN 327076-82-4, entered Mar. 14, 2001.
STN Registry Database, RN 327076-84-6, entered Mar. 14, 2001.
STN Registry Database, RN 340212-10-4, entered Jun. 10, 2001.
STN Registry Database, RN 367469-20-3, entered Nov. 7, 2001.
STN Registry Database, RN 372973-07-4, entered Dec. 3, 2001.
STN Registry Database, RN 374092-98-5, entered Dec. 6, 2001.
STN Registry Database, RN 374601-46-4, entered Dec. 10, 2001.
STN Registry Database, RN 374601-67-9, entered Dec. 10, 2001.
STN Registry Database, RN 374697-43-5, entered Dec. 11, 2001.
STN Registry Database, RN 444567-77-5, entered Nov. 1, 2004.
STN Registry Database, RN 524732-67-0, entered Jun. 3, 2003.
STN Registry Database, RN 663203-03-0, entered Mar. 15, 2004.
STN Registry Database, RN 675864-84-3, entered Apr. 16, 2004.
STN Registry Database, RN 773082-62-5, entered Nov. 1, 2004.
STN Registry Database, RN 780812-59-1, entered Nov. 15, 2004.
STN Registry Database, RN 885523-21-7, entered May 25, 2006.
STN Registry Database, RN 890353-24-9, entered Jul. 3, 2006.
STN Registry Database, RN 890353-32-9, entered Jul. 3, 2006.
STN Registry Database, RN 891362-96-2, entered Jul. 10, 2006.
STN Registry Database, RN 891363-10-3, entered Jul. 10, 2006.
STN Registry Database, RN 891379-65-0, entered Jul. 10, 2006.
STN Registry Database, RN 891379-71-8, entered Jul. 10, 2006.
STN Registry Database, RN 891379-78-5, entered Jul. 10, 2006.
STN Registry Database, RN 891563-66-9, entered Jul. 10, 2006.
STN Registry Database, RN 891569-68-9, entered Jul. 10, 2006.
STN Registry Database, RN 891569-89-4, entered Jul. 10, 2006.
STN Registry Database, RN 891569-97-4, entered Jul. 10, 2006.
STN Registry Database, RN 891590-88-8, entered Jul. 10, 2006.
STN Registry Database, RN 891590-96-8, entered Jul. 10, 2006.
STN Registry Database, RN 891591-04-1, entererd Jul. 10, 2006.
STN Registry Database, RN 891614-21-4, entered Jul. 10, 2006.
STN Registry Database, RN 891631-78-0, entered Jul. 10, 2006.
STN Registry Database, RN 891631-85-9, entered Jul. 10, 2006.
STN Registry Database, RN 894162-80-2, entered Jul. 18, 2006.
STN Registry Database, RN 894305-60-3, entered Jul. 19, 2006.
STN Registry Database, RN 895052-18-3, entered Jul. 23, 2006.
STN Registry Database, RN 903047-29-0, entered Aug. 21, 2006.
STN Registry Database, RN 904139-33-9, entered Aug. 24, 2006.
STN Registry Database, RN 904203-99-2, entered Aug. 24, 2006.
Extended European Search Report for Application No. 28132522.3 dated Dec. 11, 2023.
Extended European Search Report for EP Application No. 21832044.8 dated Dec. 7, 2023.
Zhou et al., "Structure-based discovery of new maternal embryonic leucine zipper kinase inhibitors", Organic & Biomolecular Chemistry, vol. 16, No. 9, pp. 1489-1495 (2018).
Amin et al., "Exploring structural requirements of unconventional Knoevenagel-type indole derivatives as anticancer agents through comparative QSAR modeling approaches," Can J Chemistry, 94(7):637-644 (2016).
Brennan et al., "The Allosteric Site on SHP2's Protein Tyrosine Phosphatase Domain is Targetable with Druglike Small Molecules," ACS Omega, 3(11): 15763-15770 (2018).
CAS Registry No. 891610-48-3: CA Index Name "2-Propenamide, 2-cyano-3-[1-[[3-(trifluoromethyl)phenyl]methyl]-1H-indol-3-yl]-" STN International: 3 pages (2006).
CAS Registry No. 1332531-33-5, Entered STN: Sep. 15, 2011.
CAS Registry No. 891614-21-4, Entered STN: Jul. 10, 2006.
CAS Registry No. 907553-40-6, Entered STN: Sep. 19, 2006.
CAS Registry No. 925549-16-2, Entered STN: Mar. 8, 2007.
CAS Registry No. 374601-67-9, Entered STN: Dec. 10, 2001.
CAS Registry No. 677327-34-3; CA Index Name: 2-Propenamide, 2-cyano-N-ethyl-3-(1H-pyrrolo[2,3-b]pyridin-3-yl)-; Entered STN: Apr. 28, 2004.
CAS Registry No. 1025594-30-2, Entered STN:Jun. 5, 2008.
CAS Registry No. 1232821-01-0, Entered STN:Jul. 19, 2010.
CAS Registry No. 1246086-21-4, Entered STN:Oct. 12, 2010.
CAS Registry No. 1360583-75-0, Entered STN:Mar. 9, 2012.
CAS Registry No. 1360583-78-3, Entered STN:Mar. 9, 2012.
CAS Registry No. 1417368-01-4, Entered STN:Jan. 23, 2013.
CAS Registry No. 1993738-37-6, Entered STN:Sep. 16, 2016.
CAS Registry No. 1993795-68-8, Entered STN:Sep. 16, 2016.
CAS Registry No. 2022941-63-3, Entered STN:Nov. 2, 2016.
CAS Registry No. 2094959-90-5, Entered STN:May 5, 2017.
CAS Registry No. 677327-34-3, Entered STN:Apr. 28, 2004.
CAS Registry No. 895303-82-9, Entered STN:Jul. 23, 2006.
CAS Registry No. 895304-22-0, Entered STN:Jul. 23, 2006.
CAS Registry No. 904141-89-5, Entered STN: Aug. 24, 2006.
Castilho et al., "mTOR Mediates Wnt-Induced Epidermal Stem Cell Exhaustion and Aging," Cell Stem Cell, 5(3): 279-289 (25 pages)(2009).
Choi et al., "The effect of cilostazol, a phosphodiesterase 3 (PDE3) inhibitor, on human hair growth with the dual promoting mechanisms," Journal of Dermatological Science, 91: 60-68 (2018).
El Maatougui et al., "Supported TBD-Assisted Solution Phase Diversification of Formyl-Aza-Heterocycles Through Alkylation-

(56) References Cited

OTHER PUBLICATIONS

Knoevenagel One Pot Sequences," Combinatorial Chemistry & High Throughput Screening, 14: 570-582 (2011).
Extended European Search Report for EP Application No. 17844520.1 mailed Jul. 21, 2020.
Extended European Search Report for EP Application No. 18823621 mailed Jun. 15, 2021.
Extended European Search Report for EP Application No. 18862674.1 dated Jun. 18, 2021.
Fischer et al., "Effect of caffeine and testosterone on the proliferation of human hair follicles in vitro ," International Journal of Dermatology, 46: 27-35 (2007).
Flores et al., "Inhibition of pyruvate oxidation as a versatile stimulator of the hair cycle in models of alopecia," Experimental Dermatology, 30: 448-456 (2021).
Flores et al., "Lactate dehydrogenase activity drives hair follicle stem cell activation," Nature Cell Biology, 19(9): 1017-1026 ( 2017).
Hickey et al., "Demodectic Mange in a Tamarin (*Saguinus geoffroyi*) 1,2," Laboratory Animal Science, American Associate for Laboratory Animal Science, 33(1): 192-193 (1983).
Hong et al., "Synthesis of double D-A branched organic dyes employing indole and phenoxazine as donors for efficient DSSCs," Tetrahedron, 70(36): 6296-6302 (2014).
International Preliminary Report on Patentability for International Application No. PCT/US2018/040385 mailed Dec. 31, 2019.
International Search Report and Written Opinion for International Application No. PCT/US2017/048701 dated Nov. 6, 2017.
International Search Report and Written Opinion for International Application No. PCT/US2018/040385 dated Oct. 21, 2018.
International Search Report and Written Opinion for International Application No. PCT/US2018/053351 mailed Dec. 31, 2018.
International Search Report and Written Opinion for International Application No. PCT/US2019/068905 dated Apr. 6, 2020.
International Search Report and Written Opinion for International Application No. PCT/US2020/066078 dated Mar. 25, 2021.
International Search Report and Written Opinion for International Application No. PCT/US2021/039501 mailed Sep. 30, 2021.
International Search Report and Written Opinion for International Application No. PCT/US2021/039502 mailed Sep. 30, 2021.
Issue Notification for U.S. Appl. No. 16/627,630 dated Apr. 6, 2022.
Jelinek et al., "Mapping Metabolism: Monitoring Lactate Dehydrogenase Activity Directly in Tissue," Journal of Visualized Experiments, 136: 57760 (2018).
Keren et al., "The PDE4 inhibitor, apremilast, suppresses experimentally induced alopecia areata in human skin in vivo," Journal of Dermatological Science, 77: 71-81 (2015).
Khan et al., "Arylindoles. II. N-Arylindole-3-carboxaldehydes and Their Derivatives," Chemical and Pharmaceutical Bulletin, 27(2): 528-531 (1979).
Liu et al., "Development of Novel Mitochondrial Pyruvate Carrier Inhibitors to Treat Hair Loss," Joournal of Medicinal Chemistry, 64: 2046-2063 (2021).
Liu et al., "Identification of novel thiadiazoloacrylamide analogues as inhibitors of dengue-2 virus NS2B/NS3 protease," Bioorg Med Chem, 22(22):6344-6352 (2014).
Magar et al., "Synthesis of Some Novel 3-Substituted Indole Derivatives Using Polyamine Functionalized Heterogeneous Catalyst," Journal of Heterocyclic Chemistry, 52(6): 1684-1692 (2015).
McCommis et al., "Mitochondrial pyruvate transport: a historical perspective and future research directions," Biochem J, 466(3):443-454 (2015).
Miranda et al., "Topical Inhibition of the Electron Transport Chain Can Stimulate the Hair Cycle," Journal of Investigative Dermatology, 138(4):9680972 (2017).
Miranda et al., "Topical Inhibition of the Electron Transport Chain Can Stimulate the Hair Cycle," Journal of Investigative Dermatology, 138: 968-972 (2018).
Notice of Allowance for U.S. Appl. No. 17/584,091 dated Apr. 14, 2022.
Partial Supplementary European Search Report for EP Application No. EP 18823621 dated Mar. 15, 2021.
PubChem CID 6438504; "2-Cyano-3-(1-phenylindol-3-yl)acrylate," National Library of Medicine: 18 pages (Create date Apr. 28, 2006).
Sarifakioglu., "Determination of the sildenafil effect on alopecia areata in childhood: An open-pilot comparison study," Journal of Dermatological Treatment, 17(4): 235-237 (2006).
Shan et al., "Phenanthroline-tBuOK Promoted Intramolecular C—H Arylation of Indoles with ArI under Transition-Metal-Free Conditions," Organic Letters, 20(24): 7898-7901 (2018).
Shearman et al., "The concentration of the mitochondrial pyruvate carrier in rat liver and heart mitochondria determined with a-cyano-ß-(1-phenylindol-3-yl)acrylate," Biochemical Journal 223(3): 673-676 (1984).
Taylor et al., "Src tyrosine kinsase activity in rat thecal--interstitial cells and mouse TM3 Leydig cells is positively associated with cAMP-specific phosphodiesterase activity," Molecular and Cellular Endocrinology, 126: 91-100 (1997).
Valdenaire et al., "Evolution of novel tricyclic CRTh2 receptor antagonists from a (E)-2-cyano-3-(1H-indol-3-yl)acrylamide scaffold," Bioorganic & Medicinal Chemistry Letters, 23(4): 944-948 (2013).
Vishnyakova et al., "Possible role of autophagy activation in stimulation of regeneration," Mol Biol, 47(5):692-700 (2013).
Wang et al., "Oxidative stress and substance P mediate psychological stress-induced autophagy and delay of hair growth in mice," Arch. Dermatol. Res. 307: 171-181 (2015).
Yakhontov et al., "Pyrrolo[2,3-b]pyridine derivatives (7-azaindoles) viii. Synthesis and some reactions of 4-methyl-1-phenyl-1h-4-methyl-1-phynyl-1 h-pyrrol0[2,3-b]pyridine-3-carboxaldehydel," All-Union Chem Pharma Res Int, translated from Zhurnal Obshchei Khimii 34(8):2603-2610 (1964).
Starosyla et al., "Discovery of novel protein kinase FGFR1 inhibitors using pharmacophore modeling," Ukrainica Bioorganica Acta, 13(1): 13-20 w/ English Abstract (2015).
Babu et al., "From Molecular Design to Co-sensitization; High performance indole based photosensitizers for dye-sensitized solar cells," Electrochimica Acta 198 (2016): 10-21.
CAS Registry No. 94331-28-9. Jan. 21, 1985.
Yadav et al., "Phosphane-catalyzed Knoevenagel condensation: A facile synthesis of a-cyanoacrylates and a-cyanoacrylonitriles." European Journal of Organic Chemistry (2004): 546-551.
Database Registry CAS, RN 79246-44-9, Entered STN: Nov. 16, 1984.

* cited by examiner

SYNTHESIS OF COMPOUNDS TO PROMOTE HAIR GROWTH

RELATED APPLICATIONS

This application is the § 371 National Stage of International Application No.: PCT/US2020/066078, filed Dec. 18, 2020, which claims the benefit of U.S. Provisional Patent Application No. 62/951,667, filed on Dec. 20, 2019; the contents of each application are hereby incorporated by reference in their entirety.

BACKGROUND

Hair follicle stem cells (HFSCs) undergo successive rounds of quiescence (telogen) punctuated by brief periods of proliferation correlating with the start of the hair cycle (telogen-anagen transition). Proliferation or activation of HFSCs is well known to be a prerequisite for advancement of the hair cycle. Recent advances in treatment options have identified a number of small-molecule MPC inhibitors that can modulate the hair cycle. However, new methods of synthesizing these compounds are needed.

SUMMARY OF THE INVENTION

In certain aspects, the present disclosure provides methods for the preparation of a compound of formula (I)

(I)

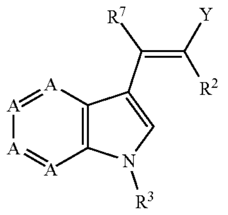

wherein:

each A is independently CH, $CR^4$, or N;

Y is carboxyl, ester, amide, or

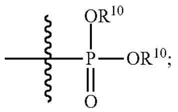

$R^2$ is CN or carboxyl;

$R^3$ is H, aryl, aralkyl, or aralkylacyl, and is optionally substituted by one or more $R^5$;

each instance of $R^4$ is independently alkyl, carboxyl, halo, hydroxy, ester, or CN;

each instance of $R^5$ is independently selected from alkyl, alkoxy, or halo;

$R^7$ is hydrogen, alkyl, halo, hydroxyl, alkoxy, or acyloxy; and $R^{10}$ is hydrogen or alkyl;

or a pharmaceutically acceptable salt thereof;

said method comprising:

reacting a compound of formula (Ic) with an acylation (e.g., formylation) reagent to produce a compound of formula (Id):

(Ic)

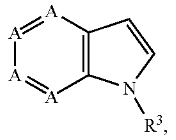

(Id)

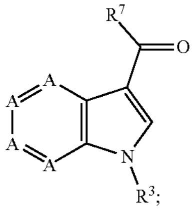

and reacting the compound of formula (Id) with a condensation agent of formula (Ie) to produce the compound of formula (I):

(Ie)

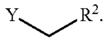

DETAILED DESCRIPTION OF THE INVENTION

Hair follicle stem cells (HFSCs) are quiescent, long-lived cells that are responsible for maintaining the cellular homeostasis of the follicle. While normally dormant, HFSCs quickly become activated to divide during a new hair cycle. The quiescence of HFSCs is known to be regulated by a number of intrinsic and extrinsic mechanisms.

Compounds have been developed that are capable of modulating these mechanisms and promoting hair growth by, for example, inhibiting MPC. Such compounds and related disclosures may be found in, for example, PCT Publication No. WO2018039612, PCT Publication No. WO2019006359, and U.S. Provisional Application No. 62/787609, now international application PCT/US019/068905, published as WO2020/142413, each of which is hereby incorporated by reference as if fully set forth herein, in particular for the MPC inhibiting compounds disclosed therein.

Thus, in certain aspects, the present disclosure provides methods for synthesizing compounds, as further described herein. In one aspect, the present disclosure provides methods for the preparation of a compound of formula (I)

(I)

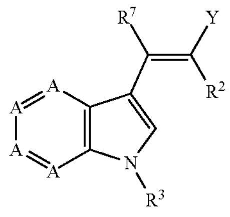

wherein:

each A is independently CH, $CR^4$, or N;

Y is carboxyl, ester, amide, or

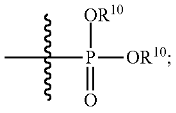

$R^2$ is CN or carboxyl;

$R^3$ is H, aryl, aralkyl, or aralkylacyl, and is optionally substituted by one or more $R^5$;

each instance of $R^4$ is independently alkyl, carboxyl, halo, hydroxy, ester, or CN;

each instance of $R^5$ is independently selected from alkyl, alkoxy, or halo;

$R^7$ is hydrogen, alkyl, halo, hydroxyl, alkoxy, or acyloxy; and $R^{10}$ is hydrogen or alkyl;

or a pharmaceutically acceptable salt thereof;

said method comprising:

reacting a compound of formula (Ic) with an acylation (e.g., formylation) reagent to produce a compound of formula (Id):

(Ic)

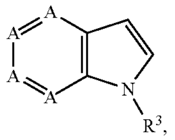

(Id)

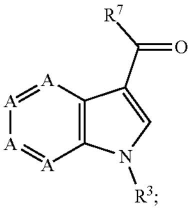

and reacting the compound of formula (Id) with a condensation agent of formula (Ie) to produce the compound of formula (I):

(Ie)

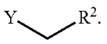

In certain embodiments, the methods described herein further comprise hydrolyzing the compound of formula (I) to produce a compound of formula (If):

(If)

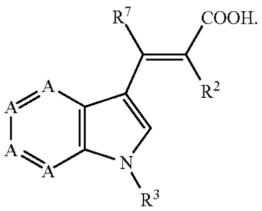

In certain embodiments, the methods described herein further comprise reacting a compound of formula (Ia) with an alkylation regent of formula (Ib) to produce a compound of formula (Ic):

(Ia)

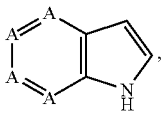

(Ib)

$R^3$—W, wherein W is a leaving group (e.g., halo).

In certain embodiments, at least one A is N. In certain preferred embodiments, exactly one A is N.

In certain preferred embodiments, the compound of formula (Ia) is

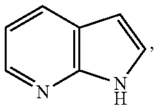

and the compounds of formulas (Ic), (Id), (I), and (If) include the corresponding heterocycles.

In certain embodiments, the compound of formula (Ia) is

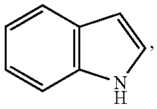

and the compounds of formulas (Ic), (Id), (I), and (If) include the corresponding heterocycles.

In certain embodiments, $R^2$ is CN.

In certain embodiments, $R^3$ is benzyl. In certain embodiments, $R^3$ is benzyl and is substituted by one or more $R^5$. In certain preferred embodiments, $R^3$ is substituted by one or two $R^5$, and wherein each $R^5$ is independently selected from fluoroalkyl or fluoro. In certain even further preferred embodiments, $R^3$ is substituted by two $R^5$, and wherein each $R^5$ is trifluoromethyl.

In certain embodiments, $R^7$ is hydrogen, hydroxyl, halo (e.g., chloro), or acyloxy (e.g., acetyloxy). In certain preferred embodiments, $R^7$ is hydrogen.

In certain embodiments, the leaving group W of the alkylation regent is halo. In certain preferred embodiments, the leaving group W of the alkylation regent is bromide.

In certain embodiments, the alkylation regent is

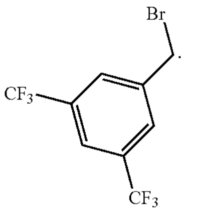 [SMILES: FC(F)(F)c1cc(CBr)cc(C(F)(F)F)c1]

In certain embodiments, the acylation reagent is phosphorus oxychloride.

In certain embodiments, the condensation agent is ethyl 2-cyanoacetate or tert-butyl 2-cyanoacetate. In certain such embodiments, the compound of formula (I) is

JXL082

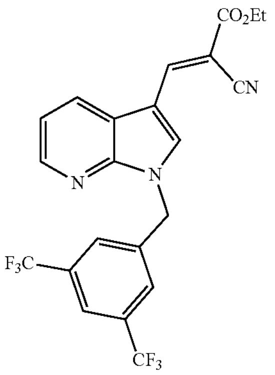

or

4

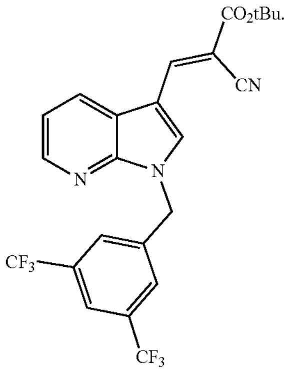

In certain embodiments, the compound of formula (If) is

JXL069

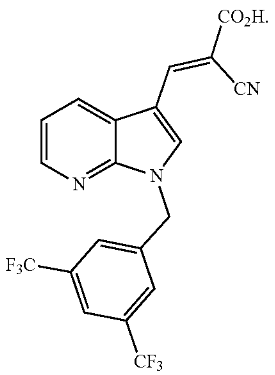

The aforementioned methods may be utilized by the skilled artisan to arrive at the compounds described below (e.g., the compounds of formula A, B, and C) using starting materials and techniques available to the skilled artisan.

In certain embodiments, the present disclosure provides methods, as further described herein, of preparing compounds according to formula (A):

(A)

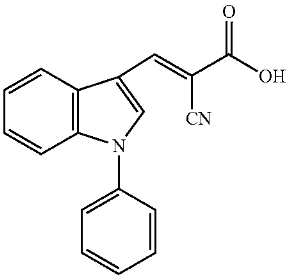

or a pharmaceutically acceptable salt thereof.

Further embodiments of formula A are provided in PCT Publication No. WO 2018/039612.

In certain embodiments, the present disclosure provides methods, as further described herein, of preparing compounds according to formula (B):

(B)

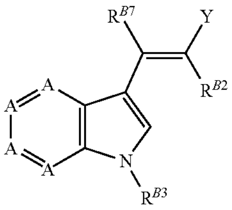

wherein:

each A is independently CH, $CR^{B4}$, or N;

Y is carboxyl, ester, amide, or

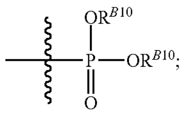

Z is CH, $CR^{B4}$, or N.

$R^{B2}$ is CN or carboxyl;

$R^{B3}$ is H, aryl, aralkyl, or aralkylacyl, and is optionally substituted by one or more $R^{B5}$, wherein each $R^{B5}$ is independently selected from alkyl, alkoxy, or halo;

each instance of $R^{B4}$ is independently alkyl, carboxyl, halo, hydroxy, ester, or CN;

$R^{B6}$ is from H, alkyl, or cycloalkyl;

$R^{B7}$ is hydrogen, alkyl, halo, hydroxyl, alkoxy, or acyloxy;

$R^{B10}$ is hydrogen or alkyl; and n is 0-4;

or a pharmaceutically acceptable salt thereof.

In certain embodiments, the present disclosure provides methods of preparing compounds according to formula BI:

(BI)

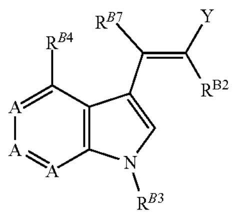

wherein,

Y is carboxyl, ester, amide, or

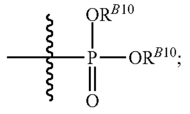

$R^{B2}$ is CN or carboxyl;

$R^{B3}$ is H, aryl, aralkyl, or aralkylacyl, and is optionally substituted by one or more $R^{B5}$, wherein each $R^{B5}$ is independently selected from alkyl, alkoxy, or halo;

each instance of $R^{B4}$ is independently alkyl, carboxyl, halo, hydroxy, ester, or CN;

$R^{B6}$ is from H, alkyl, or cycloalkyl; and $R^{B7}$ is hydrogen, alkyl, halo, hydroxyl, alkoxy, or acyloxy;

$R^{B10}$ is hydrogen or alkyl;

$R^{B11}$ is hydrogen or alkyl; and n is 0-4;

or a pharmaceutically acceptable salt thereof.

In certain embodiments of Formula B or BI, Y is wherein Y is

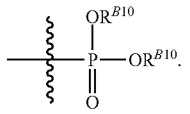

In certain embodiments, $R^{B10}$ is H. In certain embodiments, $R^{B10}$ is alkyl (e.g., ethyl). In certain embodiments Y is ester or amido.

In certain embodiments of Formula B or BI, $R^{B11}$ is alkyl (e.g., methyl).

In certain embodiments, the present disclosure provides compounds of formula BII:

(BII)

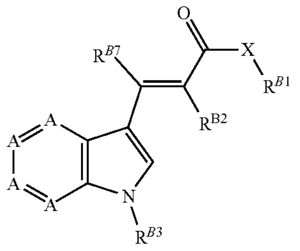

wherein:

each A is independently CH, $CR^{B4}$, or N;

X is $NR^{B6}$ or O;

$R^{B1}$ is H or lower alkyl; or either $R^{B1}$ and $R^{B6}$ or $R^{B1}$ and $R^{B2}$, together with the atoms that separate them, complete a heterocycle;

$R^{B2}$ is CN or carboxyl;

$R^{B3}$ is H, aryl, aralkyl, or aralkylacyl, and is optionally substituted by one or more $R^{B5}$, wherein each $R^{B5}$ is independently selected from alkyl, alkoxy, and halo;

each instance of $R^{B4}$ is independently alkyl, carboxyl, halo, hydroxy, or CN;

$R^{B6}$ is from H, alkyl, or cycloalkyl; and $R^{B7}$ is hydrogen, alkyl, halo, hydroxyl, alkoxy, or acyloxy;

or a pharmaceutically acceptable salt thereof.

In certain embodiments of formula B, BI, or BII, at least one A is N, preferably no more than two occurrences of A are N. In certain preferred embodiments, exactly one A is N, preferably the A bound to the same carbon as $NR^{B3}$.

In certain embodiments, the present disclosure provides compounds of formula BIII:

(BIII)

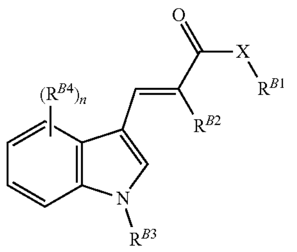

wherein:

X is $NR^{B6}$ or O;

$R^{B1}$ is H or lower alkyl;

$R^{B2}$ is CN or carboxyl; or $R^{B1}$ and $R^{B2}$, together with the atoms that separate them, complete a heterocycle;

$R^{B3}$ is H, phenyl, or benzyl, and is optionally substituted by one or more $R^{B5}$, wherein each $R^{B5}$ is independently selected from alkyl, alkoxy, or halo;

each instance of $R^{B4}$ is independently selected from alkyl, carboxyl, halo, hydroxy, or CN; and $R^{B6}$ is selected from H, alkyl, or cycloalkyl;

and pharmaceutically acceptable salts thereof.

In certain embodiments of formula B, BI, BII, or BIII, X is NH. In certain embodiments, X is O.

In certain embodiments of formula B, BI, BII, or BIII, $R^{B1}$ is H. In certain embodiments, $R^{B1}$ is lower alkyl. In certain embodiments, $R^{B1}$ and $R^{B6}$, together with the atoms that separate them, complete a heterocycle (e.g., morpholinyl).

In certain embodiments of formula B, BI, BII, or BIII, $R^{B6}$ is hydrogen.

In certain embodiments of formula V B, BI, BII, or BIII, $R^{B2}$ is CN. In certain embodiments, $R^{B2}$ is carboxyl. In certain embodiments, $R^{B1}$ and $R^{B2}$, together with the atoms that separate them, complete a heterocyclyl selected from thiazolidine-2,4-dion-5-ylidene or 2-iminothiazolidin-4-one-5-ylidene.

In certain embodiments of formula B, BI, BII, or BIII, $R^{B3}$ is H. In certain embodiments, $R^{B3}$ is phenyl. In certain embodiments, $R^{B3}$ is phenyl and is substituted by one or more $R^{B5}$. In certain embodiments, $R^{B3}$ is substituted by one $R^{B5}$, and wherein $R^{B5}$ is an alkoxy. In certain embodiments, $R^{B3}$ is aralkyl (e.g., benzyl or phenethyl). In certain embodiments, $R^{B3}$ is aralkylacyl (e.g., phenylacetyl). In certain embodiments, $R^{B3}$ is benzyl. In certain embodiments, $R^{B3}$ is benzyl and is substituted by one or more $R^{B5}$. In certain embodiments, $R^{B3}$ is aralkyl (e.g., benzyl or phenethyl) and is substituted by one or more $R^{B5}$ (preferably on the phenyl ring). In certain embodiments, $R^{B3}$ is aralkylacyl (e.g., phenylacetyl), and is substituted by one or more $R^{B5}$ (preferably on the phenyl ring). In certain embodiments, $R^{B3}$ is substituted by one or two $R^{B5}$, and wherein each $R^5$ is independently selected from fluoroalkyl or fluoro. In certain embodiments, $R^{B3}$ is substituted by two $R^{B5}$, and wherein each $R^{B5}$ is trifluoromethyl.

In certain embodiments of formula B, BI, BII, or BIII, n is 0.

In certain preferred embodiments, the present disclosure provides compounds of formula BIV (BIV)

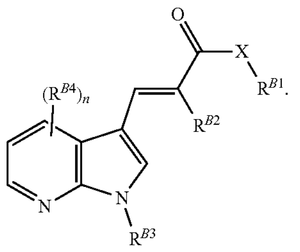

In certain embodiments, the present disclosure provides compounds of formula BV (BV)

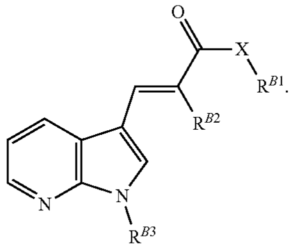

In certain embodiments of formula B, BI, BII, BIII, BIV, or BV, n is 1.

In certain preferred embodiments, the present disclosure provides compounds of formula BVI (BVI)

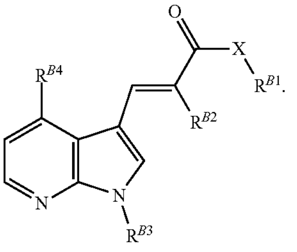

In certain embodiments, the present disclosure provides compounds of formula BVII (BVII)

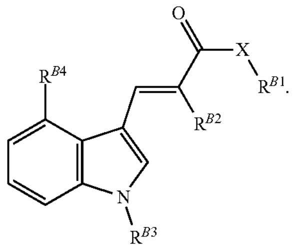

In certain embodiments of formula B, BI, BII, BIII, BIV, BV, BVI, or BVII, $R^{B4}$ is selected from halo or haloalkyl. In certain preferred embodiments, $R^{B4}$ is halo (e.g., chloro or bromo). In other preferred embodiments, $R^{B4}$ is carboxyl or ester.

In certain embodiments of formula B, BI, BII, BIII, BIV, BV, BVI, or BVII, n is 0. In certain embodiments, n is 2, and $R^{B4}$ is selected from halo or haloalkyl.

In certain embodiments of formula B, BI, BII, BIII, BIV, BV, BVI, or BVII, $R^{B7}$ is hydrogen, hydroxyl, halo (e.g., chloro), or acyloxy (e.g., acetyloxy). In certain embodiments, $R^{B7}$ is hydroxyl, halo (e.g., chloro), or acyloxy (e.g., acetyloxy).

In certain embodiments of formula B, BI, BII, BIII, BIV, BV, BVI, or BVII, the compound is not JXL001.

Further embodiments of formula B are provided in PCT Publication No. WO 2019/006359.

In certain embodiments, the present disclosure provides methods, as further described herein, of preparing compounds according to formula (C):

(C)

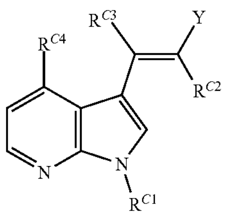

wherein:

Y is carboxyl, ester, amide, or

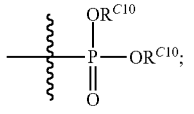

$R^{C1}$ is H, aryl, aralkyl, or aralkylacyl, and is optionally substituted by one or more $R^{C5}$;

$R^{C2}$ is CN or carboxyl;

$R^{C4}$ is independently alkyl, alkenyl, alkynyl, carboxyl, azido, halo, hydroxy, ester, or CN;

$R^{C5}$ is independently selected from alkyl, alkoxy, or halo; and n is 0-4.

In certain embodiments of formula C, Y is

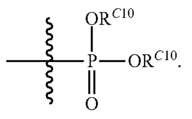

In certain such embodiments, $R^{C10}$ is H. In other such embodiments, $R^{C10}$ is alkyl (e.g., methyl, ethyl, propyl).

In other, preferred, embodiments of formula I, Y is ester or carboxyl.

In certain preferred embodiments of formula I, $R^{C2}$ is CN. In other embodiments, $R^{C2}$ is carboxyl.

In certain embodiments of formula I, $R^{C1}$ is H.

In other, preferred, embodiments of formula I, $R^{C1}$ is aralkyl (e.g., benzyl or phenethyl). In certain such embodiments, the aralkyl (e.g., benzyl or phenethyl) is substituted by one or more $R^{C5}$ (preferably on the phenyl ring). In yet other embodiments, $R^{C1}$ is aralkylacyl (e.g., phenylacetyl), and is substituted by one or more $R^{C5}$ (preferably on the phenyl ring).

In certain embodiments of formula I, $R^1$ is substituted by one or two $R^{C5}$, and wherein each $R^{C5}$ is independently selected from fluoroalkyl or fluoro. In certain preferred embodiments, $R^{C1}$ is substituted by two $R^{C5}$, and wherein each $R^{C5}$ is trifluoromethyl.

In certain embodiments of formula I, $R^{C4}$ is an electron withdrawing group. In certain embodiments, $R^{C4}$ is selected from iodo, fluoro, alkenyl (e.g., vinyl), CN, azido, alkynyl (e.g., acetylenyl), fluoroalkyl (e.g., trifluoromethyl), carboxyl, and ester (e.g., methyl ester or ethyl ester). In certain preferred embodiments, $R^{C4}$ is fluoro. In other preferred embodiments, $R^{C4}$ is ester (e.g., methyl ester or ethyl ester).

In certain embodiments, the present disclosure provides compounds of formula CIa or a pharmaceutically acceptable salt thereof:

(CIa)

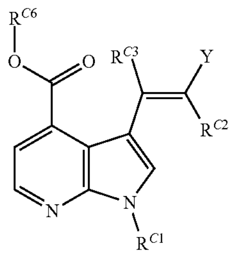

wherein $R^6$ is H, alkyl, aryl, or aralkyl.

In certain preferred embodiments of formula Ia, $R^{C6}$ is H or alkyl (e.g., methyl or ethyl).

Further embodiments of formula B are provided in PCT Publication No. WO 2020/142413.

In certain embodiments, the present disclosure provides methods of preparing a compound of Table 1:

TABLE 1

| Exemplary Compounds | |
|---|---|
| 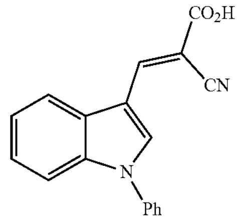 [SMILES: N#C/C(=C\c1cn(-c2ccccc2)c2ccccc12)C(=O)O] | JXL001 |
| 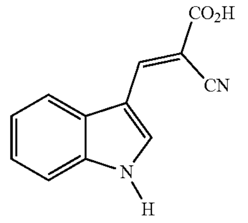 [SMILES: N#C/C(=C\c1c[nH]c2ccccc12)C(=O)O] | JXL002 |
| 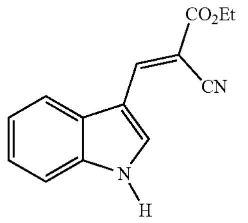 [SMILES: CCOC(=O)/C(C#N)=C/c1c[nH]c2ccccc12] | JXL003 |
| 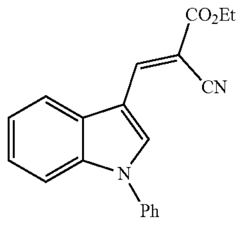 [SMILES: CCOC(=O)/C(C#N)=C/c1cn(-c2ccccc2)c2ccccc12] | JXL004 |
| 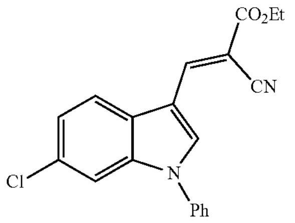 [SMILES: CCOC(=O)/C(C#N)=C/c1cn(-c2ccccc2)c2cc(Cl)ccc12] | JXL005 |
| 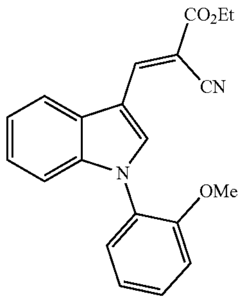 [SMILES: CCOC(=O)/C(C#N)=C/c1cn(-c2ccccc2OC)c2ccccc12] | JXL006 |

TABLE 1-continued
| Exemplary Compounds | |
|---|---|
| 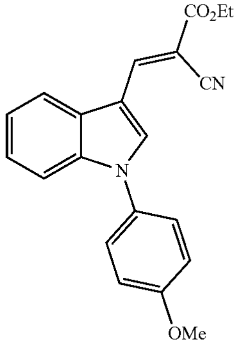 [SMILES: CCOC(=O)/C(C#N)=C/c1cn(-c2ccc(OC)cc2)c2ccccc12] | JXL007 |
| 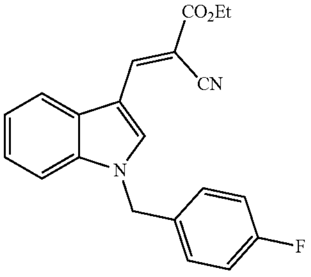 | JXL008 |
| 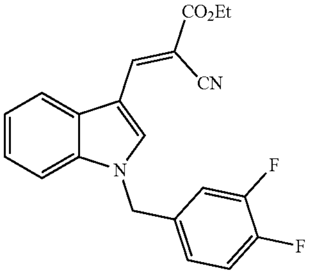 [SMILES: CCOC(=O)/C(C#N)=C/c1cn(Cc2ccc(F)c(F)c2)c2ccccc12] | JXL009 |
| 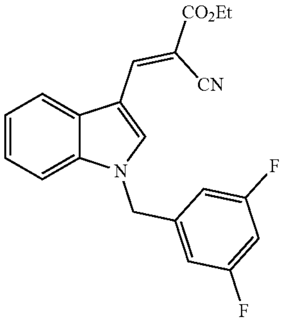 [SMILES: CCOC(=O)/C(C#N)=C/c1cn(Cc2cc(F)cc(F)c2)c2ccccc12] | JXL010 |
| 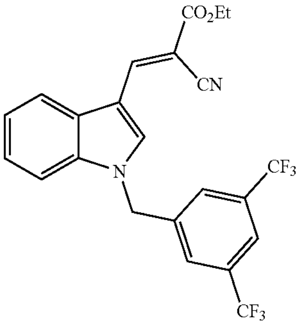 | JXL011 |
TABLE 1-continued
| Exemplary Compounds | |
|---|---|
| 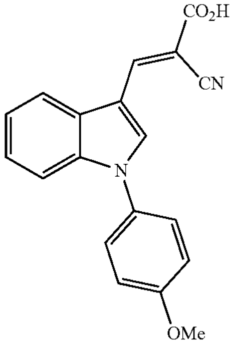 [SMILES: COc1ccc(-n2cc(/C=C(\C#N)C(=O)O)c3ccccc32)cc1] | JXL012 |
| 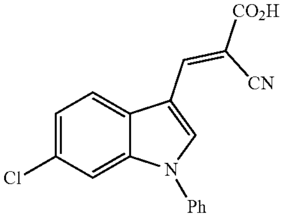 [SMILES: N#C/C(=C\c1cn(-c2ccccc2)c2cc(Cl)ccc12)C(=O)O] | JXL013 |
| 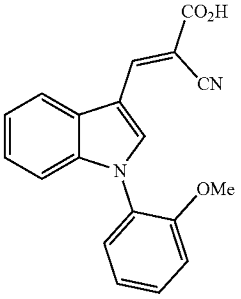 [SMILES: COc1ccccc1-n1cc(/C=C(\C#N)C(=O)O)c2ccccc21] | JXL014 |
| 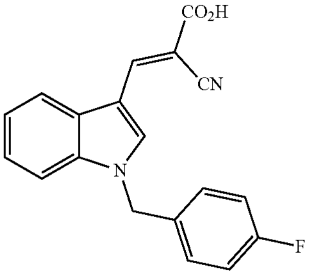 [SMILES: N#C/C(=C\c1cn(Cc2ccc(F)cc2)c2ccccc12)C(=O)O] | JXL015 |
| 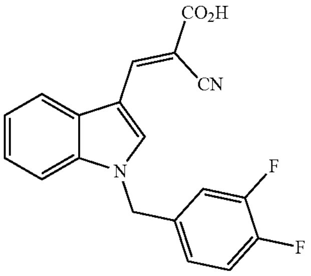 [SMILES: N#C/C(=C\c1cn(Cc2ccc(F)c(F)c2)c2ccccc12)C(=O)O] | JXL016 |

TABLE 1-continued
Exemplary Compounds
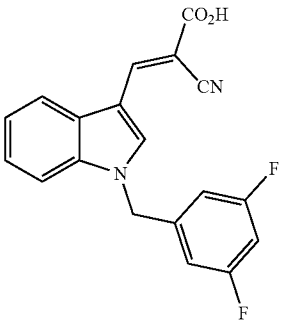 [SMILES: N#C/C(=C\c1cn(Cc2cc(F)cc(F)c2)c2ccccc12)C(=O)O]
JXL017
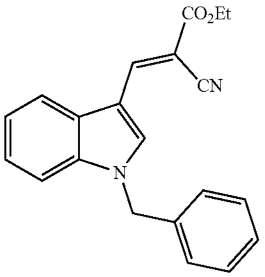 [SMILES: CCOC(=O)/C(C#N)=C/c1cn(Cc2ccccc2)c2ccccc12]
JXL018
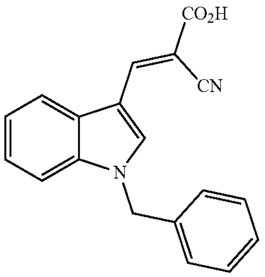 [SMILES: N#C/C(=C\c1cn(Cc2ccccc2)c2ccccc12)C(=O)O]
JXL019
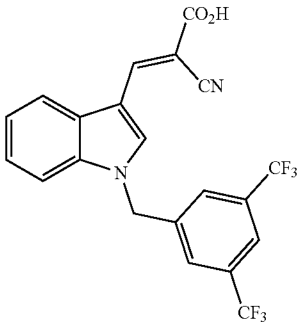 [SMILES: N#C/C(=C\c1cn(Cc2cc(C(F)(F)F)cc(C(F)(F)F)c2)c2ccccc12)C(=O)O]
JXL020
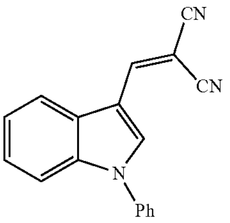 [SMILES: N#CC(C#N)=Cc1cn(-c2ccccc2)c2ccccc12]
JXL021
TABLE 1-continued
Exemplary Compounds
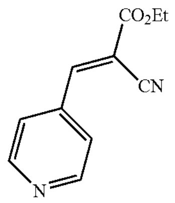 [SMILES: CCOC(=O)/C(C#N)=C/c1ccncc1]
JXL022
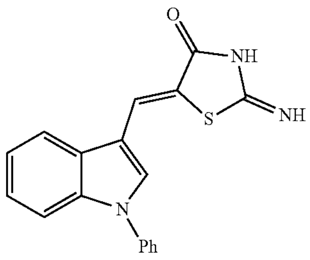 [SMILES: N=C1NC(=O)/C(=C/c2cn(-c3ccccc3)c3ccccc23)S1]
JXL023
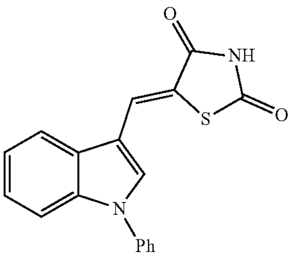 [SMILES: O=C1NC(=O)/C(=C/c2cn(-c3ccccc3)c3ccccc23)S1]
JXL024
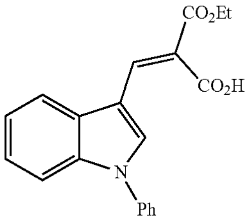 [SMILES: CCOC(=O)/C(=C/c1cn(-c2ccccc2)c2ccccc12)C(=O)O]
JXL025
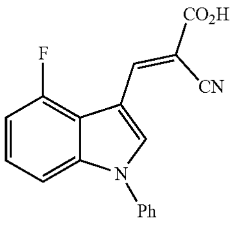 [SMILES: N#C/C(=C\c1cn(-c2ccccc2)c2cccc(F)c12)C(=O)O]
JXL026
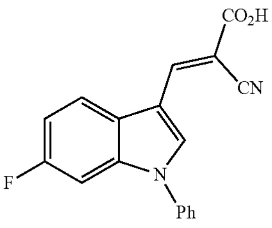 [SMILES: N#C/C(=C\c1cn(-c2ccccc2)c2cc(F)ccc12)C(=O)O]
JXL027

TABLE 1-continued
| Exemplary Compounds | |
|---|---|
| 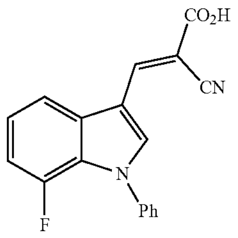 [SMILES: N#C/C(=C\c1cn(-c2ccccc2)c2c(F)cccc12)C(=O)O] | JXL028 |
| 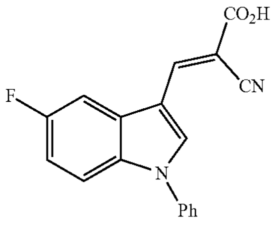 [SMILES: N#C/C(=C\c1cn(-c2ccccc2)c2ccc(F)cc12)C(=O)O] | JXL029 |
| 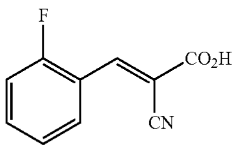 [SMILES: N#C/C(=C\c1ccccc1F)C(=O)O] | JXL030 |
| 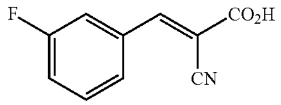 [SMILES: N#C/C(=C\c1cccc(F)c1)C(=O)O] | JXL031 |
| 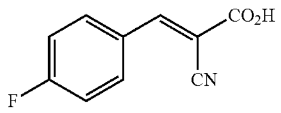 [SMILES: N#C/C(=C\c1ccc(F)cc1)C(=O)O] | JXL032 |
| 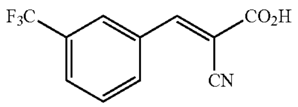 [SMILES: N#C/C(=C\c1cccc(C(F)(F)F)c1)C(=O)O] | JXL033 |
| 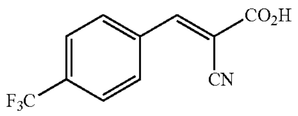 [SMILES: N#C/C(=C\c1ccc(C(F)(F)F)cc1)C(=O)O] | JXL034 |
| 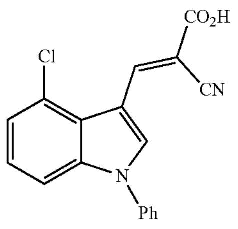 [SMILES: N#C/C(=C\c1cn(-c2ccccc2)c2cccc(Cl)c12)C(=O)O] | JXL035 |
TABLE 1-continued
| Exemplary Compounds | |
|---|---|
| 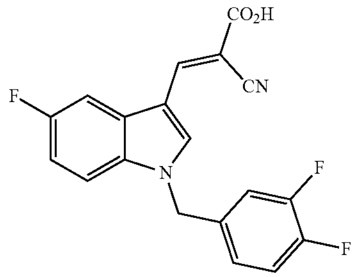 [SMILES: N#C/C(=C\c1cn(Cc2ccc(F)c(F)c2)c2ccc(F)cc12)C(=O)O] | JXL036 |
| 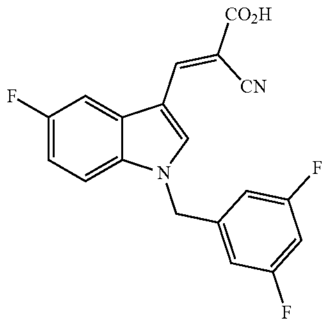 [SMILES: N#C/C(=C\c1cn(Cc2cc(F)cc(F)c2)c2ccc(F)cc12)C(=O)O] | JXL037 |
| 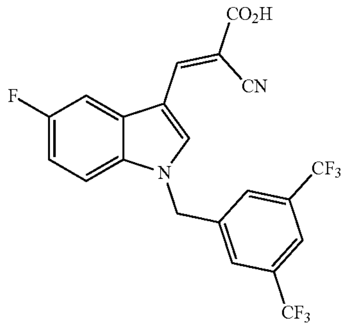 [SMILES: N#C/C(=C\c1cn(Cc2cc(C(F)(F)F)cc(C(F)(F)F)c2)c2ccc(F)cc12)C(=O)O] | JXL038 |
| 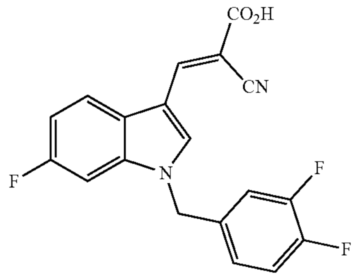 [SMILES: N#C/C(=C\c1cn(Cc2ccc(F)c(F)c2)c2cc(F)ccc12)C(=O)O] | JXL039 |
| 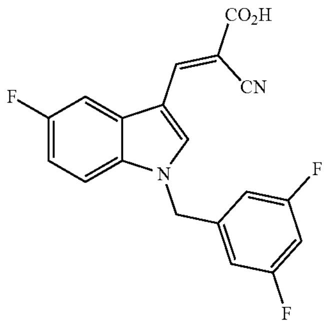 [SMILES: N#C/C(=C\c1cn(Cc2cc(F)cc(F)c2)c2ccc(F)cc12)C(=O)O] | JXL040 |

TABLE 1-continued
| Exemplary Compounds | |
|---|---|
| 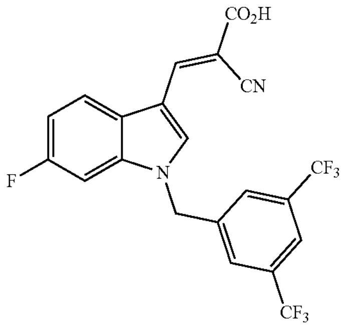 [SMILES: N#C/C(=C\c1cn(Cc2cc(C(F)(F)F)cc(C(F)(F)F)c2)c2cc(F)ccc12)C(=O)O] | JXL041 |
| 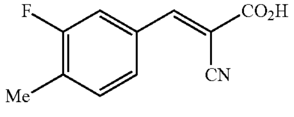 [SMILES: Cc1ccc(/C=C(\C#N)C(=O)O)cc1F] | JXL042 |
| 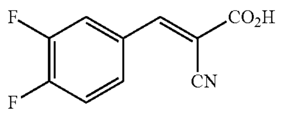 [SMILES: N#C/C(=C\c1ccc(F)c(F)c1)C(=O)O] | JXL043 |
| 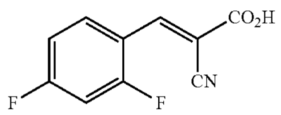 [SMILES: N#C/C(=C\c1ccc(F)cc1F)C(=O)O] | JXL044 |
| 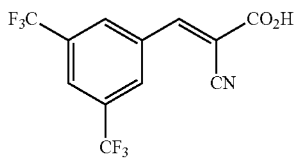 [SMILES: N#C/C(=C\c1cc(C(F)(F)F)cc(C(F)(F)F)c1)C(=O)O] | JXL045 |
| 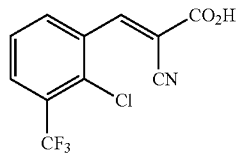 [SMILES: N#C/C(=C\c1cccc(C(F)(F)F)c1Cl)C(=O)O] | JXL046 |
| 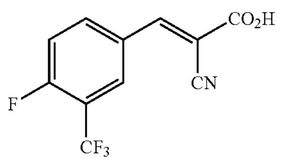 [SMILES: N#C/C(=C\c1ccc(F)c(C(F)(F)F)c1)C(=O)O] | JXL047 |
| 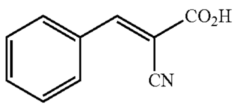 [SMILES: N#C/C(=C\c1ccccc1)C(=O)O] | JXL048 |
| 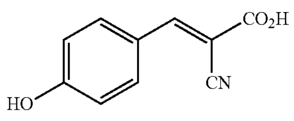 [SMILES: N#C/C(=C\c1ccc(O)cc1)C(=O)O] | JXL049 |
TABLE 1-continued
| Exemplary Compounds | |
|---|---|
| 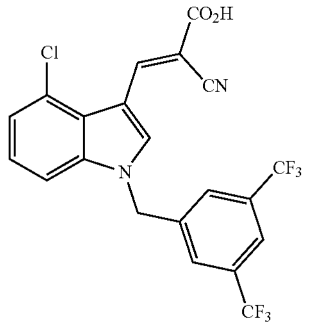 | JXL050 |
| 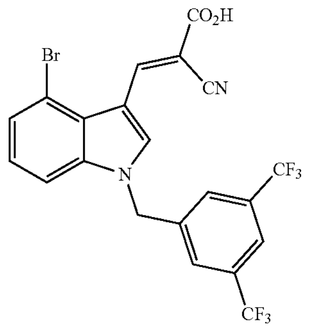 | JXL051 |
| 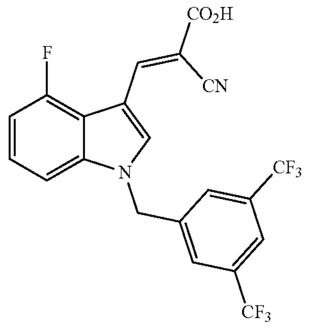 | JXL052 |
| 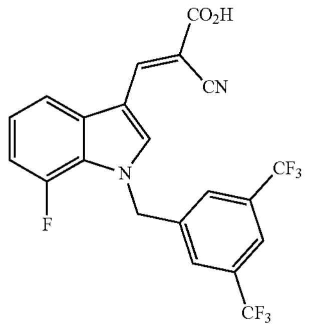 [SMILES: N#C/C(=C\c1cn(Cc2cc(C(F)(F)F)cc(C(F)(F)F)c2)c2c(F)cccc12)C(=O)O] | JXL053 |

TABLE 1-continued
| Exemplary Compounds | |
|---|---|
| 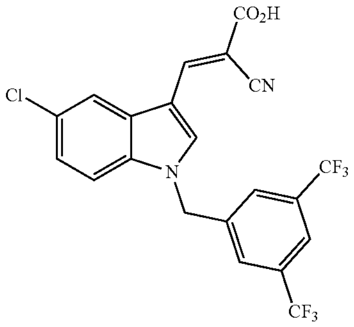 [SMILES: N#C/C(=C\c1cn(Cc2cc(C(F)(F)F)cc(C(F)(F)F)c2)c2ccc(Cl)cc12)C(=O)O] | JXL054 |
| 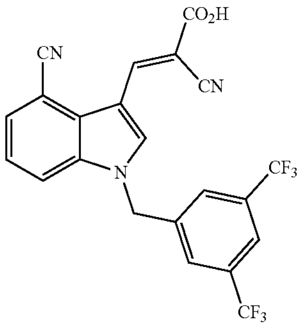 [SMILES: N#C/C(=C\c1cn(Cc2cc(C(F)(F)F)cc(C(F)(F)F)c2)c2cccc(C#N)c12)C(=O)O] | JXL055 |
| 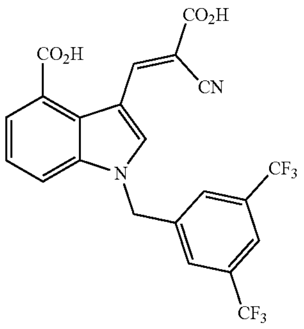 [SMILES: N#C/C(=C\c1cn(Cc2cc(C(F)(F)F)cc(C(F)(F)F)c2)c2cccc(C(=O)O)c12)C(=O)O] | JXL056 |
| 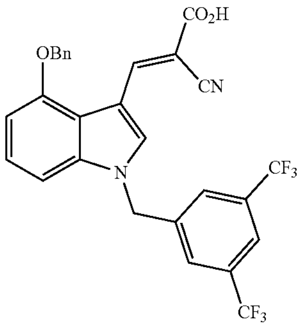 | JXL057 |
TABLE 1-continued
| Exemplary Compounds | |
|---|---|
| 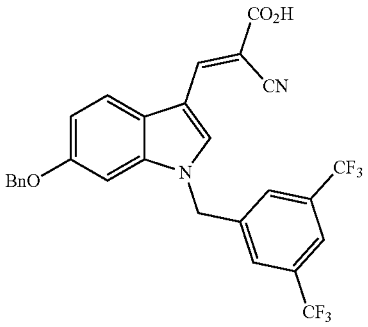 [SMILES: N#C/C(=C\c1cn(Cc2cc(C(F)(F)F)cc(C(F)(F)F)c2)c2cc(OCc3ccccc3)ccc12)C(=O)O] | JXL058 |
| 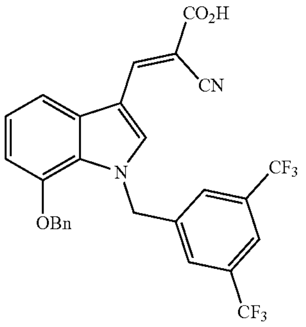 [SMILES: N#C/C(=C\c1cn(Cc2cc(C(F)(F)F)cc(C(F)(F)F)c2)c2c(OCc3ccccc3)cccc12)C(=O)O] | JXL059 |
| 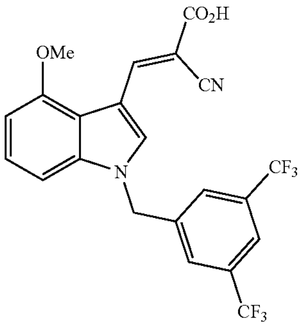 [SMILES: COc1cccc2c1c(/C=C(\C#N)C(=O)O)cn2Cc1cc(C(F)(F)F)cc(C(F)(F)F)c1] | JXL060 |
| 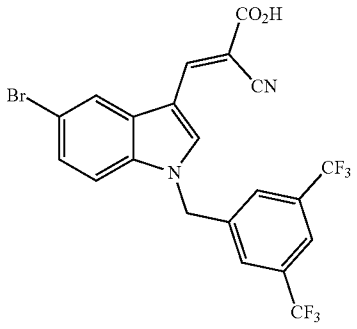 | JXL061 |

TABLE 1-continued
| Exemplary Compounds | |
|---|---|
| 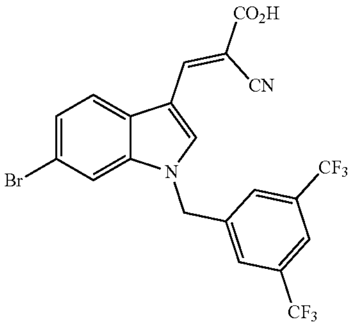 [SMILES: N#C/C(=C\c1cn(Cc2cc(C(F)(F)F)cc(C(F)(F)F)c2)c2cc(Cl)ccc12)C(=O)O] | JXL062 |
| 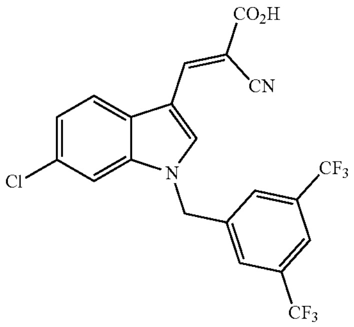 | JXL063 |
| 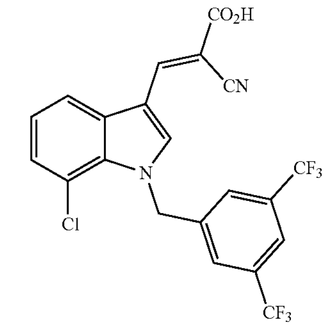 [SMILES: N#C/C(=C\c1cn(Cc2cc(C(F)(F)F)cc(C(F)(F)F)c2)c2c(Cl)cccc12)C(=O)O] | JXL064 |
| 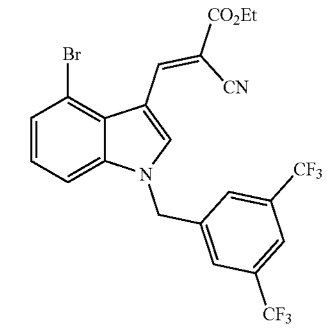 | JXL065 |
TABLE 1-continued
| Exemplary Compounds | |
|---|---|
| 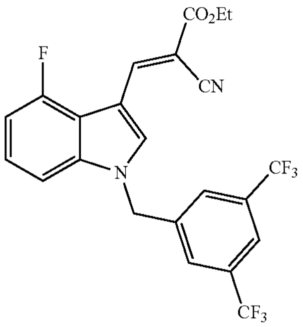 [SMILES: CCOC(=O)/C(C#N)=C/c1cn(Cc2cc(C(F)(F)F)cc(C(F)(F)F)c2)c2cccc(F)c12] | JXL066 |
| 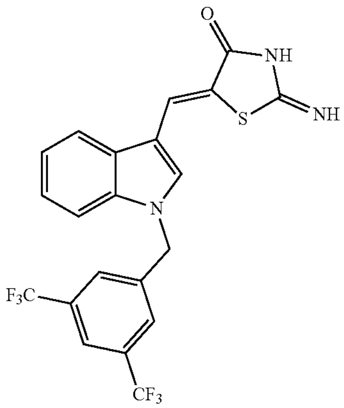 [SMILES: N=C1NC(=O)/C(=C/c2cn(Cc3cc(C(F)(F)F)cc(C(F)(F)F)c3)c3ccccc23)S1] | JXL067 |
| 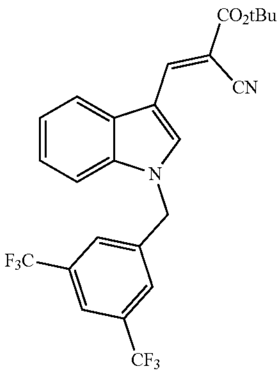 [SMILES: CC(C)(C)OC(=O)/C(C#N)=C/c1cn(Cc2cc(C(F)(F)F)cc(C(F)(F)F)c2)c2ccccc12] | JXL068 |
| 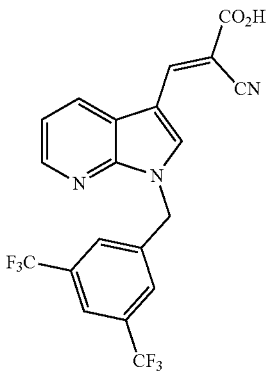 | JXL069 |

TABLE 1-continued
| Exemplary Compounds |
|---|
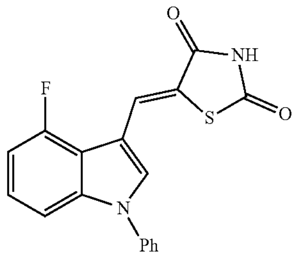 [SMILES: O=C1NC(=O)/C(=C/c2cn(-c3ccccc3)c3cccc(F)c23)S1]
JXL070
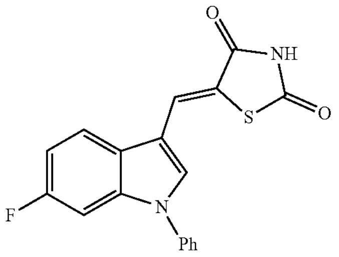 [SMILES: O=C1NC(=O)/C(=C/c2cn(-c3ccccc3)c3cc(F)ccc23)S1]
JXL071
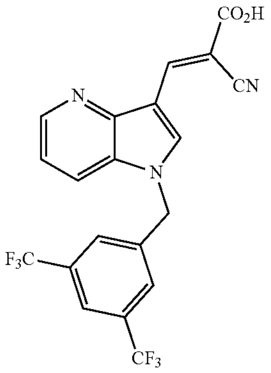
JXL072
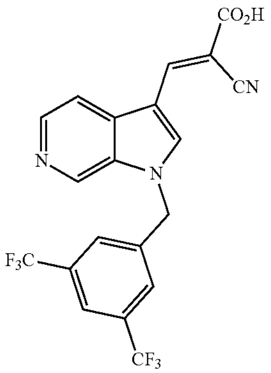 [SMILES: N#C/C(=C\c1cn(Cc2cc(C(F)(F)F)cc(C(F)(F)F)c2)c2cnccc12)C(=O)O]
JXL073
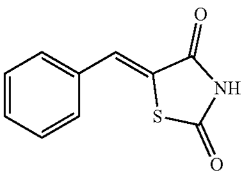 [SMILES: O=C1NC(=O)/C(=C/c2ccccc2)S1]
JXL074
TABLE 1-continued
| Exemplary Compounds |
|---|
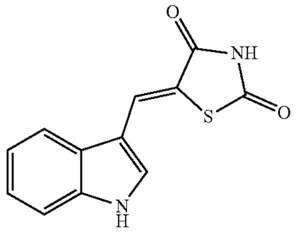 [SMILES: O=C1NC(=O)/C(=C/c2c[nH]c3ccccc23)S1]
JXL075
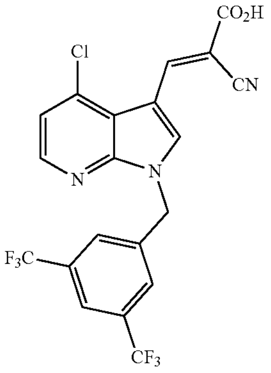
JXL076
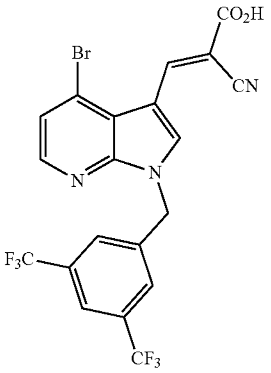
JXL077
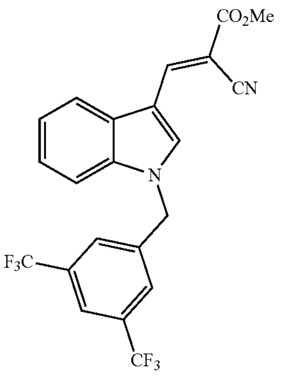
JXL078

TABLE 1-continued
| Exemplary Compounds | |
|---|---|
| 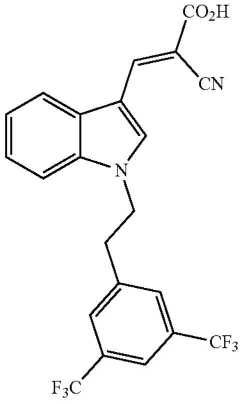 [SMILES: N#C/C(=C\c1cn(CCc2cc(C(F)(F)F)cc(C(F)(F)F)c2)c2ccccc12)C(=O)O] | JXL079 |
| 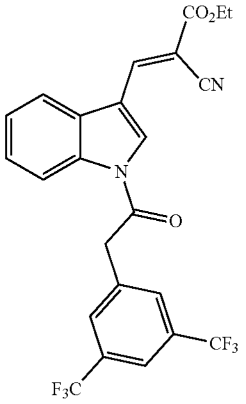 [SMILES: CCOC(=O)/C(C#N)=C/c1cn(C(=O)Cc2cc(C(F)(F)F)cc(C(F)(F)F)c2)c2ccccc12] | JXL080 |
| 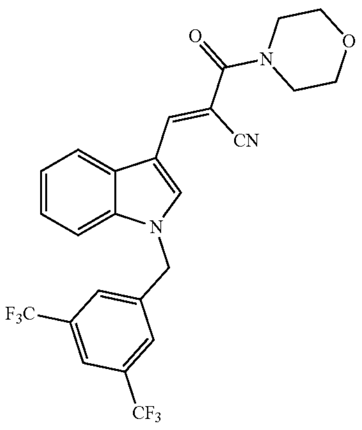 [SMILES: N#C/C(=C\c1cn(Cc2cc(C(F)(F)F)cc(C(F)(F)F)c2)c2ccccc12)C(=O)N1CCOCC1] | JXL081 |
| 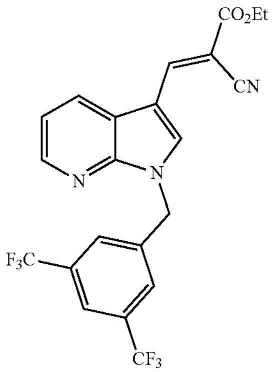 [SMILES: CCOC(=O)/C(C#N)=C/c1cn(Cc2cc(C(F)(F)F)cc(C(F)(F)F)c2)c2ncccc12] | JXL082 |
TABLE 1-continued
| Exemplary Compounds | |
|---|---|
| 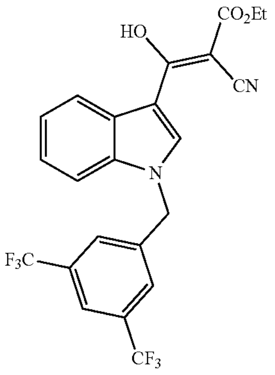 [SMILES: CCOC(=O)/C(C#N)=C(\O)c1cn(Cc2cc(C(F)(F)F)cc(C(F)(F)F)c2)c2ccccc12] | JXL083 |
| 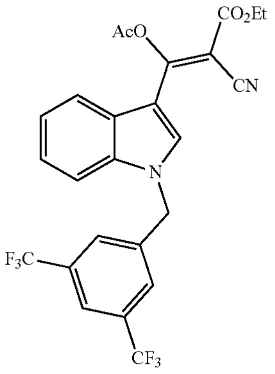 [SMILES: CCOC(=O)/C(C#N)=C(\OC(C)=O)c1cn(Cc2cc(C(F)(F)F)cc(C(F)(F)F)c2)c2ccccc12] | JXL084 |
| 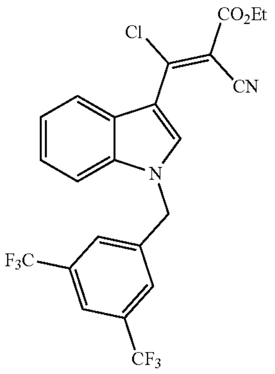 [SMILES: CCOC(=O)/C(C#N)=C(\Cl)c1cn(Cc2cc(C(F)(F)F)cc(C(F)(F)F)c2)c2ccccc12] | JXL085 |
| 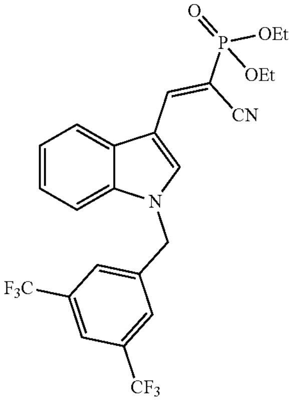 [SMILES: CCOP(=O)(OCC)/C(C#N)=C/c1cn(Cc2cc(C(F)(F)F)cc(C(F)(F)F)c2)c2ccccc12] | JXL086 |

TABLE 1-continued
| Exemplary Compounds | |
|---|---|
| 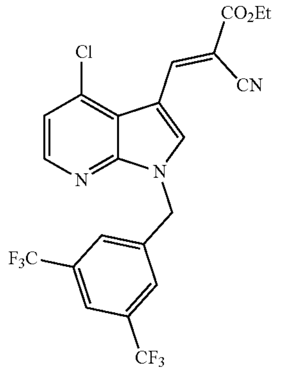 | JXL087 |
| 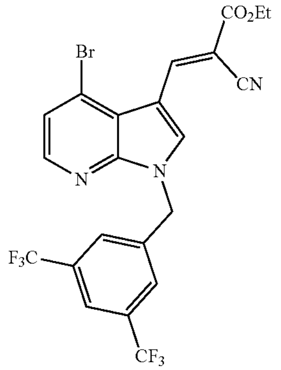 [SMILES: CCOC(=O)/C(C#N)=C/c1cn(Cc2cc(C(F)(F)F)cc(C(F)(F)F)c2)c2nccc(Br)c12] | JXL088 |
| 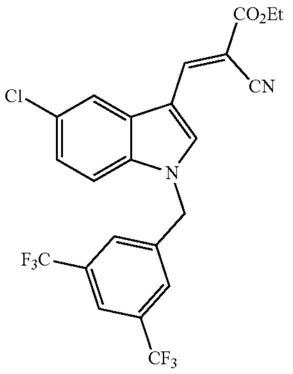 [SMILES: CCOC(=O)/C(C#N)=C/c1cn(Cc2cc(C(F)(F)F)cc(C(F)(F)F)c2)c2ccc(Cl)cc12] | JXL089 |
| 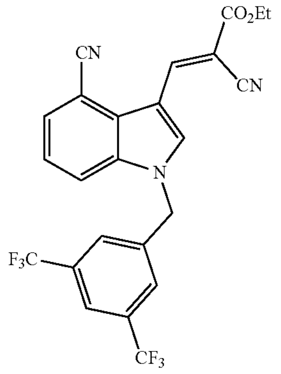 [SMILES: CCOC(=O)/C(C#N)=C/c1cn(Cc2cc(C(F)(F)F)cc(C(F)(F)F)c2)c2cccc(C#N)c12] | JXL090 |
TABLE 1-continued
| Exemplary Compounds | |
|---|---|
| 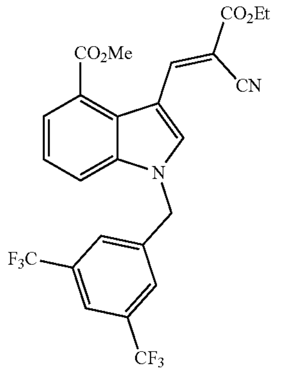 | JXL091 |
| 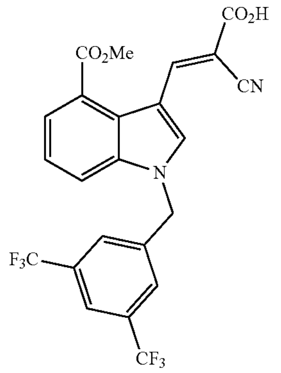 [SMILES: CCOC(=O)/C(C#N)=C/c1cn(Cc2cc(C(F)(F)F)cc(C(F)(F)F)c2)c2cccc(C(=O)OC)c12] | JXL092 |
| 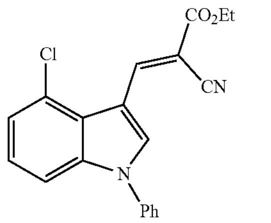 [SMILES: CCOC(=O)/C(C#N)=C/c1cn(-c2ccccc2)c2cccc(Cl)c12] | JXL093 |
| 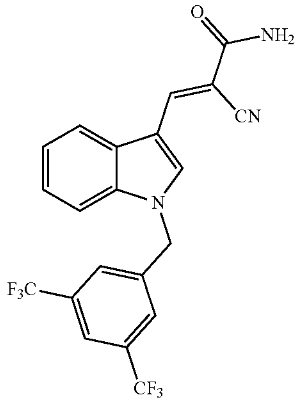 [SMILES: N#C/C(=C\c1cn(Cc2cc(C(F)(F)F)cc(C(F)(F)F)c2)c2ccccc12)C(N)=O] | JXL094 |

TABLE 1-continued

Exemplary Compounds

JXL095

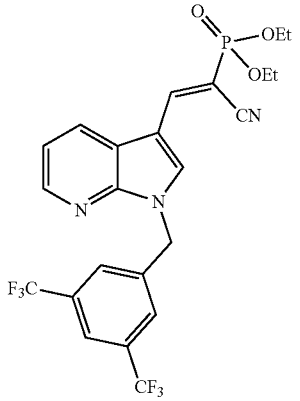

JXL096

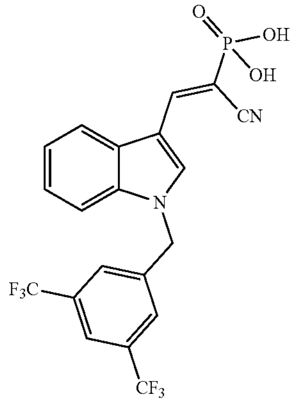 [SMILES: N#C/C(=C\c1cn(Cc2cc(C(F)(F)F)cc(C(F)(F)F)c2)c2ccccc12)P(=O)(O)O]

Pharmaceutical Compositions

The present disclosure includes the preparation and use of pharmaceutically acceptable salts of compounds prepared by the methods of the invention. In certain embodiments, contemplated salts of the invention include, but are not limited to, alkyl, dialkyl, trialkyl or tetra-alkyl ammonium salts. In certain embodiments, contemplated salts of the invention include, but are not limited to, L-arginine, benenthamine, benzathine, betaine, calcium hydroxide, choline, deanol, diethanolamine, diethylamine, 2-(diethylamino) ethanol, ethanolamine, ethylenediamine, N-methylglucamine, hydrabamine, 1H-imidazole, lithium, L-lysine, magnesium, 4-(2-hydroxyethyl)morpholine, piperazine, potassium, 1-(2-hydroxyethyl)pyrrolidine, sodium, triethanolamine, tromethamine, and zinc salts. In certain embodiments, contemplated salts of the invention include, but are not limited to, Na, Ca, K, Mg, Zn or other metal salts. In certain embodiments, contemplated salts of the invention include, but are not limited to, 1-hydroxy-2-naphthoic acid, 2,2-dichloroacetic acid, 2-hydroxyethanesulfonic acid, 2-oxoglutaric acid, 4-acetamidobenzoic acid, 4-aminosalicylic acid, acetic acid, adipic acid, 1-ascorbic acid, 1-aspartic acid, benzenesulfonic acid, benzoic acid, (+)-camphoric acid, (+)-camphor-10-sulfonic acid, capric acid (decanoic acid), caproic acid (hexanoic acid), caprylic acid (octanoic acid), carbonic acid, cinnamic acid, citric acid, cyclamic acid, dodecylsulfuric acid, ethane-1,2-disulfonic acid, ethanesulfonic acid, formic acid, fumaric acid, galactaric acid, gentisic acid, d-glucoheptonic acid, d-gluconic acid, d-glucuronic acid, glutamic acid, glutaric acid, glycerophosphoric acid, glycolic acid, hippuric acid, hydrobromic acid, hydrochloric acid, isobutyric acid, lactic acid, lactobionic acid, lauric acid, maleic acid, 1-malic acid, malonic acid, mandelic acid, methanesulfonic acid, naphthalene-1,5-disulfonic acid, naphthalene-2-sulfonic acid, nicotinic acid, nitric acid, oleic acid, oxalic acid, palmitic acid, pamoic acid, phosphoric acid, proprionic acid, 1-pyroglutamic acid, salicylic acid, sebacic acid, stearic acid, succinic acid, sulfuric acid, 1-tartaric acid, thiocyanic acid, p-toluenesulfonic acid, trifluoroacetic acid, and undecylenic acid acid salts.

The pharmaceutically acceptable acid addition salts can also exist as various solvates, such as with water, methanol, ethanol, dimethylformamide, and the like. Mixtures of such solvates can also be prepared. The source of such solvate can be from the solvent of crystallization, inherent in the solvent of preparation or crystallization, or adventitious to such solvent.

Definitions

Unless otherwise defined herein, scientific and technical terms used in this application shall have the meanings that are commonly understood by those of ordinary skill in the art. Generally, nomenclature used in connection with, and techniques of, chemistry, cell and tissue culture, molecular biology, cell and cancer biology, neurobiology, neurochemistry, virology, immunology, microbiology, pharmacology, genetics and protein and nucleic acid chemistry, described herein, are those well known and commonly used in the art.

The methods and techniques of the present disclosure are generally performed, unless otherwise indicated, according to conventional methods well known in the art and as described in various general and more specific references that are cited and discussed throughout this specification. See, e.g. "Principles of Neural Science", McGraw-Hill Medical, New York, N.Y. (2000); Motulsky, "Intuitive Biostatistics", Oxford University Press, Inc. (1995); Lodish et al., "Molecular Cell Biology, 4th ed.", W. H. Freeman & Co., New York (2000); Griffiths et al., "Introduction to Genetic Analysis, 7th ed.", W. H. Freeman & Co., N.Y. (1999); and Gilbert et al., "Developmental Biology, 6th ed.", Sinauer Associates, Inc., Sunderland, MA (2000).

Chemistry terms used herein, unless otherwise defined herein, are used according to conventional usage in the art, as exemplified by "The McGraw-Hill Dictionary of Chemical Terms", Parker S., Ed., McGraw-Hill, San Francisco, CA (1985).

All of the above, and any other publications, patents and published patent applications referred to in this application are specifically incorporated by reference herein. In case of conflict, the present specification, including its specific definitions, will control.

The term "agent" is used herein to denote a chemical compound (such as an organic or inorganic compound, a mixture of chemical compounds), a biological macromolecule (such as a nucleic acid, an antibody, including parts thereof as well as humanized, chimeric and human antibodies and monoclonal antibodies, a protein or portion thereof, e.g., a peptide, a lipid, a carbohydrate), or an extract made from biological materials such as bacteria, plants, fungi, or animal (particularly mammalian) cells or tissues. Agents include, for example, agents whose structure is known, and those whose structure is not known. The ability of such agents to inhibit AR or promote AR degradation may render them suitable as "therapeutic agents" in the methods and compositions of this disclosure.

A "patient," "subject," or "individual" are used interchangeably and refer to either a human or a non-human animal. These terms include mammals, such as humans, primates, livestock animals (including bovines, porcines, etc.), companion animals (e.g., canines, felines, etc.) and rodents (e.g., mice and rats).

"Treating" a condition or patient refers to taking steps to obtain beneficial or desired results, including clinical results. As used herein, and as well understood in the art, "treatment" is an approach for obtaining beneficial or desired results, including clinical results. Beneficial or desired clinical results can include, but are not limited to, alleviation or amelioration of one or more symptoms or conditions, diminishment of extent of disease, stabilized (i.e. not worsening) state of disease, preventing spread of disease, delay or slowing of disease progression, amelioration or palliation of the disease state, and remission (whether partial or total), whether detectable or undetectable. "Treatment" can also mean prolonging survival as compared to expected survival if not receiving treatment.

The term "preventing" is art-recognized, and when used in relation to a condition, such as a local recurrence (e.g., pain), a disease such as cancer, a syndrome complex such as heart failure or any other medical condition, is well understood in the art, and includes administration of a composition which reduces the frequency of, or delays the onset of, symptoms of a medical condition in a subject relative to a subject which does not receive the composition. Thus, prevention of cancer includes, for example, reducing the number of detectable cancerous growths in a population of patients receiving a prophylactic treatment relative to an untreated control population, and/or delaying the appearance of detectable cancerous growths in a treated population versus an untreated control population, e.g., by a statistically and/or clinically significant amount.

"Administering" or "administration of" a substance, a compound or an agent to a subject can be carried out using one of a variety of methods known to those skilled in the art. For example, a compound or an agent can be administered, intravenously, arterially, intradermally, intramuscularly, intraperitoneally, subcutaneously, ocularly, sublingually, orally (by ingestion), intranasally (by inhalation), intraspinally, intracerebrally, and transdermally (by absorption, e.g., through a skin duct). A compound or agent can also appropriately be introduced by rechargeable or biodegradable polymeric devices or other devices, e.g., patches and pumps, or formulations, which provide for the extended, slow or controlled release of the compound or agent. Administering can also be performed, for example, once, a plurality of times, and/or over one or more extended periods.

Appropriate methods of administering a substance, a compound or an agent to a subject will also depend, for example, on the age and/or the physical condition of the subject and the chemical and biological properties of the compound or agent (e.g., solubility, digestibility, bioavailability, stability and toxicity). In some embodiments, a compound or an agent is administered orally, e.g., to a subject by ingestion. In some embodiments, the orally administered compound or agent is in an extended release or slow release formulation, or administered using a device for such slow or extended release.

As used herein, the phrase "conjoint administration" refers to any form of administration of two or more different therapeutic agents such that the second agent is administered while the previously administered therapeutic agent is still effective in the body (e.g., the two agents are simultaneously effective in the patient, which may include synergistic effects of the two agents). For example, the different therapeutic compounds can be administered either in the same formulation or in separate formulations, either concomitantly or sequentially. Thus, an individual who receives such treatment can benefit from a combined effect of different therapeutic agents.

A "therapeutically effective amount" or a "therapeutically effective dose" of a drug or agent is an amount of a drug or an agent that, when administered to a subject will have the intended therapeutic effect. The full therapeutic effect does not necessarily occur by administration of one dose, and may occur only after administration of a series of doses. Thus, a therapeutically effective amount may be administered in one or more administrations. The precise effective amount needed for a subject will depend upon, for example, the subject's size, health and age, and the nature and extent of the condition being treated, such as cancer or MDS. The skilled worker can readily determine the effective amount for a given situation by routine experimentation.

The term "acyl" is art-recognized and refers to a group represented by the general formula hydrocarbylC(O)—, preferably alkylC(O)—.

The term "acylamino" is art-recognized and refers to an amino group substituted with an acyl group and may be represented, for example, by the formula hydrocarbylC(O)NH—.

The term "acyloxy" is art-recognized and refers to a group represented by the general formula hydrocarbylC(O)O—, preferably alkylC(O)O—.

The term "alkoxy" refers to an alkyl group having an oxygen attached thereto. Representative alkoxy groups include methoxy, ethoxy, propoxy, tert-butoxy and the like.

The term "alkoxyalkyl" refers to an alkyl group substituted with an alkoxy group and may be represented by the general formula alkyl-O-alkyl.

The term "alkyl" refers to saturated aliphatic groups, including straight-chain alkyl groups, branched-chain alkyl groups, cycloalkyl (alicyclic) groups, alkyl-substituted cycloalkyl groups, and cycloalkyl-substituted alkyl groups. In preferred embodiments, a straight chain or branched chain alkyl has 30 or fewer carbon atoms in its backbone (e.g., $C_{1-30}$ for straight chains, $C_{3-30}$ for branched chains), and more preferably 20 or fewer.

Moreover, the term "alkyl" as used throughout the specification, examples, and claims is intended to include both unsubstituted and substituted alkyl groups, the latter of which refers to alkyl moieties having substituents replacing a hydrogen on one or more carbons of the hydrocarbon backbone, including haloalkyl groups such as trifluoromethyl and 2,2,2-trifluoroethyl, etc.

The term "$C_{x-y}$" or "$C_x$-$C_y$", when used in conjunction with a chemical moiety, such as, acyl, acyloxy, alkyl, alkenyl, alkynyl, or alkoxy is meant to include groups that contain from x to y carbons in the chain. $C_0$alkyl indicates a hydrogen where the group is in a terminal position, a bond if internal. A $C_{1-6}$alkyl group, for example, contains from one to six carbon atoms in the chain.

The term "alkylamino", as used herein, refers to an amino group substituted with at least one alkyl group.

The term "alkylthio", as used herein, refers to a thiol group substituted with an alkyl group and may be represented by the general formula alkylS-.

The term "amide", as used herein, refers to a group

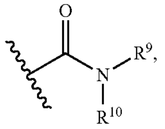

wherein $R^9$ and $R^{10}$ each independently represent a hydrogen or hydrocarbyl group, or $R^9$ and $R^{10}$ taken together with the N atom to which they are attached complete a heterocycle having from 4 to 8 atoms in the ring structure.

The terms "amine" and "amino" are art-recognized and refer to both unsubstituted and substituted amines and salts thereof, e.g., a moiety that can be represented by

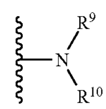
or
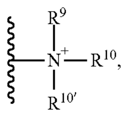

wherein $R^9$, $R^{10}$, and $R^{10'}$ each independently represent a hydrogen or a hydrocarbyl group, or $R^9$ and $R^{10}$ taken together with the N atom to which they are attached complete a heterocycle having from 4 to 8 atoms in the ring structure.

The term "aminoalkyl", as used herein, refers to an alkyl group substituted with an amino group.

The term "aralkyl", as used herein, refers to an alkyl group substituted with an aryl group.

The term "aryl" as used herein include substituted or unsubstituted single-ring aromatic groups in which each atom of the ring is carbon. Preferably the ring is a 5- to 7-membered ring, more preferably a 6-membered ring. The term "aryl" also includes polycyclic ring systems having two or more cyclic rings in which two or more carbons are common to two adjoining rings wherein at least one of the rings is aromatic, e.g., the other cyclic rings can be cycloalkyls, cycloalkenyls, cycloalkynyls, aryls, heteroaryls, and/or heterocyclyls. Aryl groups include benzene, naphthalene, phenanthrene, phenol, aniline, and the like.

The term "carbamate" is art-recognized and refers to a group

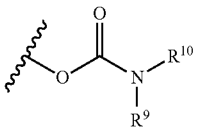
or
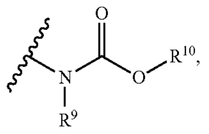

wherein $R^9$ and $R^{10}$ independently represent hydrogen or a hydrocarbyl group.

The term "carbocyclylalkyl", as used herein, refers to an alkyl group substituted with a carbocycle group.

The terms "carbocycle", "carbocyclyl", and "carbocyclic", as used herein, refers to a non-aromatic saturated or unsaturated ring in which each atom of the ring is carbon. Preferably a carbocycle ring contains from 3 to 10 atoms, more preferably from 5 to 7 atoms.

The term "carbocyclylalkyl", as used herein, refers to an alkyl group substituted with a carbocycle group.

The term "carbonate" is art-recognized and refers to a group $—OCO_2—$.

The term "carboxy", as used herein, refers to a group represented by the formula $—CO_2H$.

The term "ester", as used herein, refers to a group $—C(O)OR^9$ wherein $R^9$ represents a hydrocarbyl group.

The term "ether", as used herein, refers to a hydrocarbyl group linked through an oxygen to another hydrocarbyl group. Accordingly, an ether substituent of a hydrocarbyl group may be hydrocarbyl-O—. Ethers may be either symmetrical or unsymmetrical. Examples of ethers include, but are not limited to, heterocycle-O-heterocycle and aryl-O-heterocycle. Ethers include "alkoxyalkyl" groups, which may be represented by the general formula alkyl-O-alkyl.

The terms "halo" and "halogen" as used herein means halogen and includes chloro, fluoro, bromo, and iodo.

The terms "hetaralkyl" and "heteroaralkyl", as used herein, refers to an alkyl group substituted with a hetaryl group.

The terms "heteroaryl" and "hetaryl" include substituted or unsubstituted aromatic single ring structures, preferably 5- to 7-membered rings, more preferably 5- to 6-membered rings, whose ring structures include at least one heteroatom, preferably one to four heteroatoms, more preferably one or two heteroatoms. The terms "heteroaryl" and "hetaryl" also include polycyclic ring systems having two or more cyclic rings in which two or more carbons are common to two adjoining rings wherein at least one of the rings is heteroaromatic, e.g., the other cyclic rings can be cycloalkyls, cycloalkenyls, cycloalkynyls, aryls, heteroaryls, and/or heterocyclyls. Heteroaryl groups include, for example, pyrrole, furan, thiophene, imidazole, oxazole, thiazole, pyrazole, pyridine, pyrazine, pyridazine, and pyrimidine, and the like.

The term "heteroatom" as used herein means an atom of any element other than carbon or hydrogen. Preferred heteroatoms are nitrogen, oxygen, and sulfur.

The term "heterocyclylalkyl", as used herein, refers to an alkyl group substituted with a heterocycle group.

The terms "heterocyclyl", "heterocycle", and "heterocyclic" refer to substituted or unsubstituted non-aromatic ring structures, preferably 3- to 10-membered rings, more preferably 3- to 7-membered rings, whose ring structures include at least one heteroatom, preferably one to four heteroatoms, more preferably one or two heteroatoms. The terms "heterocyclyl" and "heterocyclic" also include polycyclic ring systems having two or more cyclic rings in which two or more carbons are common to two adjoining rings wherein at least one of the rings is heterocyclic, e.g., the other cyclic rings can be cycloalkyls, cycloalkenyls, cycloalkynyls, aryls, heteroaryls, and/or heterocyclyls. Heterocyclyl groups include, for example, piperidine, piperazine, pyrrolidine, morpholine, lactones, lactams, and the like.

The term "hydrocarbyl", as used herein, refers to a group that is bonded through a carbon atom that does not have a =O or =S substituent, and typically has at least one carbon-hydrogen bond and a primarily carbon backbone, but may optionally include heteroatoms. Thus, groups like methyl, ethoxyethyl, 2-pyridyl, and even trifluoromethyl are considered to be hydrocarbyl for the purposes of this application, but substituents such as acetyl (which has a =O substituent on the linking carbon) and ethoxy (which is linked through oxygen, not carbon) are not. Hydrocarbyl groups include, but are not limited to aryl, heteroaryl, carbocycle, heterocycle, alkyl, alkenyl, alkynyl, and combinations thereof.

The term "hydroxyalkyl", as used herein, refers to an alkyl group substituted with a hydroxy group.

The term "lower" when used in conjunction with a chemical moiety, such as, acyl, acyloxy, alkyl, alkenyl, alkynyl, or alkoxy is meant to include groups where there are ten or fewer atoms in the substituent, preferably six or fewer. A "lower alkyl", for example, refers to an alkyl group that contains ten or fewer carbon atoms, preferably six or fewer. In certain embodiments, acyl, acyloxy, alkyl, alkenyl, alkynyl, or alkoxy substituents defined herein are respectively lower acyl, lower acyloxy, lower alkyl, lower alkenyl, lower alkynyl, or lower alkoxy, whether they appear alone or in combination with other substituents, such as in the recitations hydroxyalkyl and aralkyl (in which case, for example, the atoms within the aryl group are not counted when counting the carbon atoms in the alkyl substituent).

The terms "polycyclyl", "polycycle", and "polycyclic" refer to two or more rings (e.g., cycloalkyls, cycloalkenyls, cycloalkynyls, aryls, heteroaryls, and/or heterocyclyls) in which two or more atoms are common to two adjoining rings, e.g., the rings are "fused rings". Each of the rings of the polycycle can be substituted or unsubstituted. In certain embodiments, each ring of the polycycle contains from 3 to 10 atoms in the ring, preferably from 5 to 7.

The term "sulfate" is art-recognized and refers to the group —$OSO_3H$, or a pharmaceutically acceptable salt thereof.

The term "sulfonamide" is art-recognized and refers to the group represented by the general formulae

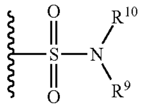 or 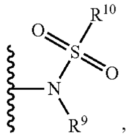 , wherein $R^9$ and $R^{10}$ independently represents hydrogen or hydrocarbyl.

The term "sulfoxide" is art-recognized and refers to the group —S(O)—.

The term "sulfonate" is art-recognized and refers to the group $SO_3H$, or a pharmaceutically acceptable salt thereof.

The term "sulfone" is art-recognized and refers to the group —$S(O)_2$—.

The term "substituted" refers to moieties having substituents replacing a hydrogen on one or more carbons of the backbone. It will be understood that "substitution" or "substituted with" includes the implicit proviso that such substitution is in accordance with permitted valence of the substituted atom and the substituent, and that the substitution results in a stable compound, e.g., which does not spontaneously undergo transformation such as by rearrangement, cyclization, elimination, etc. As used herein, the term "substituted" is contemplated to include all permissible substituents of organic compounds. In a broad aspect, the permissible substituents include acyclic and cyclic, branched and unbranched, carbocyclic and heterocyclic, aromatic and non-aromatic substituents of organic compounds. The permissible substituents can be one or more and the same or different for appropriate organic compounds. For purposes of this invention, the heteroatoms such as nitrogen may have hydrogen substituents and/or any permissible substituents of organic compounds described herein which satisfy the valences of the heteroatoms. Substituents can include any substituents described herein, for example, a halogen, a hydroxyl, a carbonyl (such as a carboxyl, an alkoxycarbonyl, a formyl, or an acyl), a thiocarbonyl (such as a thioester, a thioacetate, or a thioformate), an alkoxyl, a phosphoryl, a phosphate, a phosphonate, a phosphinate, an amino, an amido, an amidine, an imine, a cyano, a nitro, an azido, a sulfhydryl, an alkylthio, a sulfate, a sulfonate, a sulfamoyl, a sulfonamido, a sulfonyl, a heterocyclyl, an aralkyl, or an aromatic or heteroaromatic moiety. It will be understood by those skilled in the art that the moieties substituted on the hydrocarbon chain can themselves be substituted, if appropriate.

The term "thioalkyl", as used herein, refers to an alkyl group substituted with a thiol group.

The term "thioester", as used herein, refers to a group —$C(O)SR^9$ or —$SC(O)R^9$ wherein $R^9$ represents a hydrocarbyl.

The term "thioether", as used herein, is equivalent to an ether, wherein the oxygen is replaced with a sulfur.

The term "urea" is art-recognized and may be represented by the general formula

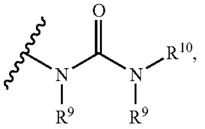

wherein $R^9$ and $R^{10}$ independently represent hydrogen or a hydrocarbyl.

The term "modulate" as used herein includes the inhibition or suppression of a function or activity (such as cell proliferation) as well as the enhancement of a function or activity.

The phrase "pharmaceutically acceptable" is art-recognized. In certain embodiments, the term includes compositions, excipients, adjuvants, polymers and other materials and/or dosage forms which are, within the scope of sound medical judgment, suitable for use in contact with the tissues of human beings and animals without excessive toxicity, irritation, allergic response, or other problem or complication, commensurate with a reasonable benefit/risk ratio.

"Pharmaceutically acceptable salt" or "salt" is used herein to refer to an acid addition salt or a basic addition salt which is suitable for or compatible with the treatment of patients.

The term "pharmaceutically acceptable acid addition salt" as used herein means any non-toxic organic or inorganic salt of any base compounds represented by Formula I. Illustrative inorganic acids which form suitable salts include hydrochloric, hydrobromic, sulfuric and phosphoric acids, as well as metal salts such as sodium monohydrogen orthophosphate and potassium hydrogen sulfate. Illustrative organic acids that form suitable salts include mono-, di-, and tricarboxylic acids such as glycolic, lactic, pyruvic, malonic, succinic, glutaric, fumaric, malic, tartaric, citric, ascorbic, maleic, benzoic, phenylacetic, cinnamic and salicylic acids, as well as sulfonic acids such as p-toluene sulfonic and methanesulfonic acids. Either the mono or di-acid salts can be formed, and such salts may exist in either a hydrated, solvated or substantially anhydrous form. In general, the acid addition salts of compounds of Formula I are more soluble in water and various hydrophilic organic solvents, and generally demonstrate higher melting points in comparison to their free base forms. The selection of the appropriate salt will be known to one skilled in the art. Other non-pharmaceutically acceptable salts, e.g., oxalates, may be used, for example, in the isolation of compounds of Formula I for laboratory use, or for subsequent conversion to a pharmaceutically acceptable acid addition salt.

The term "pharmaceutically acceptable basic addition salt" as used herein means any non-toxic organic or inorganic base addition salt of any acid compounds represented by Formula I or any of their intermediates. Illustrative inorganic bases which form suitable salts include lithium, sodium, potassium, calcium, magnesium, or barium hydroxide. Illustrative organic bases which form suitable salts include aliphatic, alicyclic, or aromatic organic amines such as methylamine, trimethylamine and picoline or ammonia. The selection of the appropriate salt will be known to a person skilled in the art.

Many of the compounds useful in the methods and compositions of this disclosure have at least one stereogenic center in their structure. This stereogenic center may be present in a R or a S configuration, said R and S notation is used in correspondence with the rules described in Pure Appl. Chem. (1976), 45, 11-30. The disclosure contemplates all stereoisomeric forms such as enantiomeric and diastereoisomeric forms of the compounds, salts, prodrugs or mixtures thereof (including all possible mixtures of stereoisomers). See, e.g., WO 01/062726.

Furthermore, certain compounds which contain alkenyl groups may exist as Z (zusammen) or E (entgegen) isomers. In each instance, the disclosure includes both mixture and separate individual isomers.

Some of the compounds may also exist in tautomeric forms. Such forms, although not explicitly indicated in the formulae described herein, are intended to be included within the scope of the present disclosure.

“Prodrug” or “pharmaceutically acceptable prodrug” refers to a compound that is metabolized, for example hydrolyzed or oxidized, in the host after administration to form the compound of the present disclosure (e.g., compounds of formula I). Typical examples of prodrugs include compounds that have biologically labile or cleavable (protecting) groups on a functional moiety of the active compound. Prodrugs include compounds that can be oxidized, reduced, aminated, deaminated, hydroxylated, dehydroxylated, hydrolyzed, dehydrolyzed, alkylated, dealkylated, acylated, deacylated, phosphorylated, or dephosphorylated to produce the active compound. Examples of prodrugs using ester or phosphoramidate as biologically labile or cleavable (protecting) groups are disclosed in U.S. Pat. Nos. 6,875,751, 7,585,851, and 7,964,580, the disclosures of which are incorporated herein by reference. The prodrugs of this disclosure are metabolized to produce a compound of Formula I. The present disclosure includes within its scope, prodrugs of the compounds described herein. Conventional procedures for the selection and preparation of suitable prodrugs are described, for example, in “Design of Prodrugs” Ed. H. Bundgaard, Elsevier, 1985.

The phrase “pharmaceutically acceptable carrier” as used herein means a pharmaceutically acceptable material, composition or vehicle, such as a liquid or solid filter, diluent, excipient, solvent or encapsulating material useful for formulating a drug for medicinal or therapeutic use.

The term “Log of solubility”, “LogS” or “logS” as used herein is used in the art to quantify the aqueous solubility of a compound. The aqueous solubility of a compound significantly affects its absorption and distribution characteristics. A low solubility often goes along with a poor absorption. LogS value is a unit stripped logarithm (base 10) of the solubility measured in mol/liter.

EXAMPLES

The invention now being generally described, it will be more readily understood by reference to the following examples which are included merely for purposes of illustration of certain aspects and embodiments of the present invention, and are not intended to limit the invention.

Example 1: Synthesis of JXL082

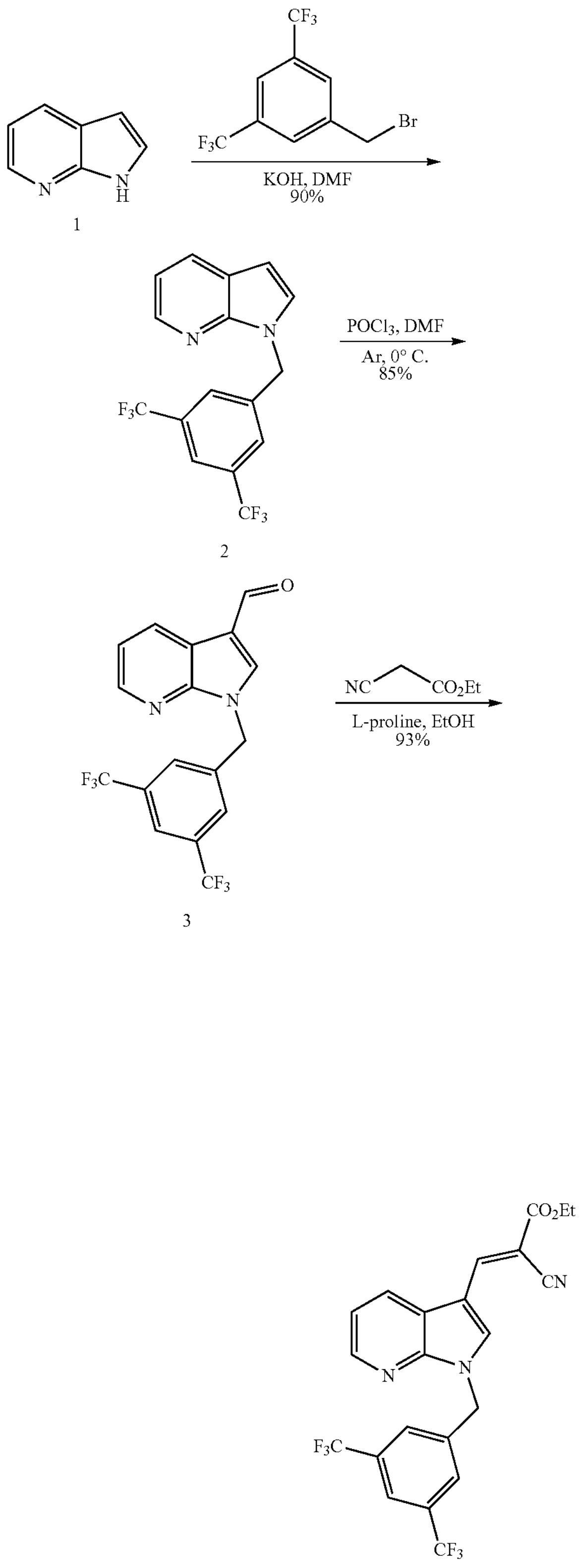

1

2

3

JXL082

1-(3,5-Bis(trifluoromethyl)benzyl)-1H-pyrrolo[2,3-b]pyridine (2)

To the solution of 7-azaindole 1 (5 mmol, 590 mg) in dry dimethylformamide (DMF, 10 mL) were added 3,5-bis(trifluoromethyl)benzyl bromide (1.2 equiv, 6 mmol, 1.32 mL) and KOH (1.2 equiv, 6 mmol, 402 mg) at 0° C. The reaction mixture was stirred at 21° C. for 2 h. After the reaction completion shown by TLC, water (30 mL) was added to the reaction vial. The reaction mixture was extracted by dichloromethane (30 mL×3). The combined organic layer was dried by sodium sulfate and concentrated. The residue was purified by flash column chromatography (hexanes:ethyl acetate=12:1) to provide the desired product 2 in 90% yield.

$^1H$ NMR (300 MHz, $CDCl_3$) δ 8.40 (d, J=4.7 Hz, 1H), 8.00 (dd, 1H, J=7.8, 1.3 Hz, 1H), 7.84 (s, 1H), 7.72 (s, 2H), 7.24 (d, J=3.5 Hz, 1H), 7.16 (dd, J=7.8, 4.7 Hz, 1H), 6.60 (d, J=3.5 Hz, 1H), 5.65 (s, 2H). $^{13}C$ NMR (126 MHz, $CDCl_3$) δ 147.6, 143.5, 140.5, 132.1 (q, Jc-f=33.6 Hz), 129.3, 127.5, 127.4, 123.1 (q, Jc-f=273.3 Hz), 121.7, 120.5, 116.4, 101.3, 47.1.

1-(3,5-Bis(trifluoromethyl)benzyl)-1H-pyrrolo[2,3-b]pyridine-3-carboxaldehyde (3)

Phosphorus oxychloride ($POCl_3$, 2 mmol, 180 μL) was added dropwise to DMF (4 mL) at 0° C. under argon. After the reaction stirred for 10 min, a solution of compound 2 (2 mmol, 668 mg) in DMF (4 mL) was added slowly with stirring. The mixture was kept at 21° C. overnight. The reaction was quenched by adding water (10 mL) at 0° C., then extracted with dichloromethane (10 mL×3). The combined organic layer was dried by sodium sulfate and concentrated. The residue was purified by flash column chromatography (hexanes:ethyl acetate=4:1) to provide the desired aldehyde 3 in 85% yield.

$^1H$ NMR (500 MHz, $CDCl_3$) δ 10.00 (s, 1H), 8.59 (d, J=7.7 Hz, 1H), 8.46 (d, J=4.6 Hz, 1H), 7.87 (s, 1H), 7.84 (s, 1H), 7.77 (s, 2H), 7.32 (dd, J=7.6, 4.8 Hz, 1H), 5.66 (s, 2H). $^{13}C$ NMR (126 MHz, $CDCl_3$) δ 184.6, 148.3, 145.7, 138.7, 136.9, 132.5 (q, Jc-f=33.6 Hz), 131.0, 128.0, 123.0 (q, Jc-f=272.8 Hz), 122.4, 119.5, 117.6, 47.9.

Ethyl (E)-3-(1-(3,5-bis(trifluoromethyl)benzyl)-1H-pyrrolo[2,3-b]pyridin-3-yl)-2-cyanoacrylate (JXL082)

To the solution of the aldehyde 3 (1 mmol, 372 mg) in ethanol (2 mL) was added ethyl 2-cyanoacetate (1.3 equiv, 1.3 mmol, 140 μL) and L-proline (40 mol %, 0.4 mmol, 58 mg). The reaction was stirred at 21° C. for 12 h and yellow solid precipitated gradually. After completion of the reaction, ice-cold water (2 mL) was added into the reaction vial. The solid was separated by Buchner funnel filtration and washed with water (2 mL×3) and dried to afford the desired product JXL082 in 93% yield.

$^1H$ NMR (500 MHz, CDC13) δ 8.64 (s, 1H), 8.51 (s, 1H), 8.48 (dd, J=4.6, 1.2 Hz, 1H), 8.21 (dd, J=7.9, 1.2 Hz, 1H), 7.83 (s, 1H), 7.77 (s, 2H), 7.34 (dd, J=7.9, 4.6 Hz, 1H), 5.69 (s, 2H), 4.38 (q, J=7.1 Hz, 2H), 1.40 (t, J=7.1 Hz, 3H) $^{13}C$ NMR (126 MHz, $CDCl_3$) δ 163.3, 147.6, 145.7, 145.0, 138.5, 132.7, 132.3 (q, Jc-f=33.6 Hz), 127.9, 127.7, 123.1 (q, Jc-f=273.3 Hz), 122.5, 120.3, 119.0, 117.6, 109.4, 97.0, 62.3, 48.3, 14.3.

Example 2: Synthesis of JXL069

Method 1

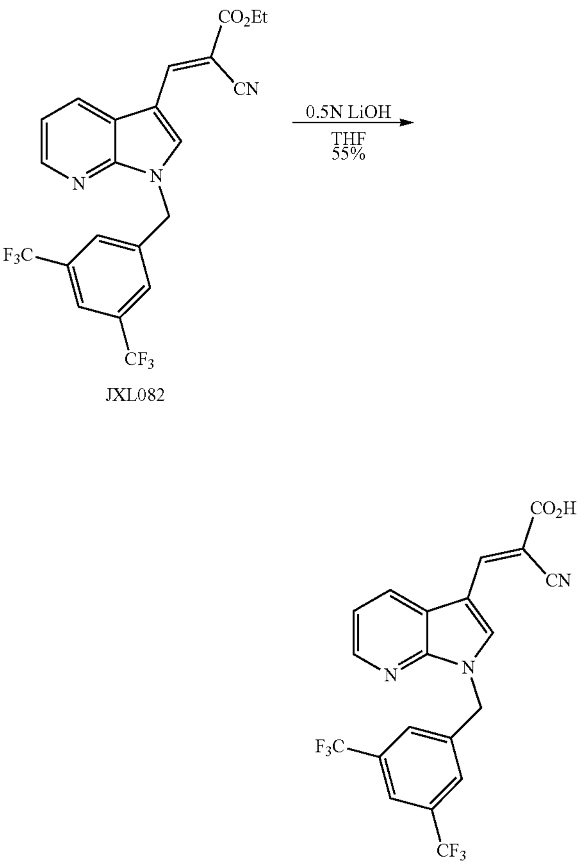

JXL082

JXL069

(E)-3-(1-(3,5-Bis(trifluoromethyl)benzyl)-1H-pyrrolo[2,3-b]pyridin-3-yl)-2-cyanoacrylic acid (JXL069)

To a solution of JXL082 (0.21 mmol, 100 mg) in THF (2 mL) was added 0.5 N LiOH solution (3 equiv, 0.4 mmol, 0.8 mL). The reaction mixture was stirred at 21° C. for 1 h. After reaction completion shown by TLC, the THF was evaporated. Concentrated HCl was added dropwise to acidify the reaction mixture until the pH was lower than 1, during which time a yellow solid precipitated. Ice-cold water (5 mL) was added to the reaction mixture and the solid was filtered using a PYREX™ Hirsch-type funnel with a fritted disc and washed with water (5 mL×3). After it was dried under vacuum, the solid was washed with 2 mL of a solvent mixture of 5:1 hexanes:ethyl acetate 5 to 10 times and monitored by TLC until non-polar impurities disappeared (the non-polar compound was the retro-aldol condensation product, 3, which can be recovered from the filtrate). Finally, the purity of the product JXL069 was checked by NMR. The product (50.7 mg) was isolated in 55% yield. See below for NMR data.

Method 2

(E)-3-(1-(3,5-Bis(trifluoromethyl)benzyl)-1H-pyrrolo[2,3-b]pyridin-3-yl)-2-cyanoacrylic acid (JXL069)

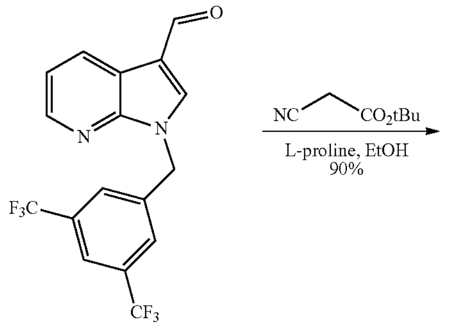

3

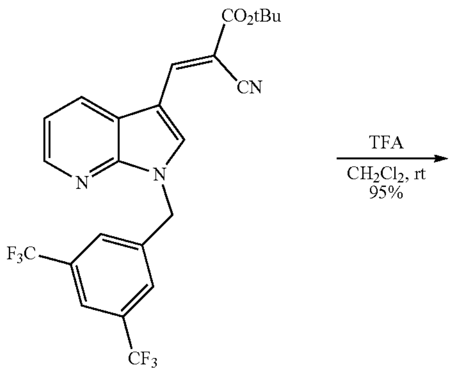

4

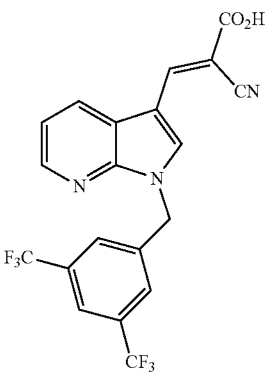

JXL069 tert-Butyl (E)-3-(1-(3,5-bis(trifluoromethyl)benzyl)-1H-pyrrolo[2,3-b]pyridin-3-yl)-2-cyanoacrylate (4)

To the solution of aldehyde 3 (1 mmol, 372 mg) in ethanol (2 mL) was added tert-butyl 2-cyanoacetate (1.3 equiv, 1.3 mmol, 183 μL) and L-proline (40 mol %, 0.4 mmol, 58 mg). The reaction was stirred at 21° C. for 12 h and a yellow solid precipitated gradually. After completion of the reaction, ice-cold water (2 mL) was added into the reaction vial. The solid was separated by Buchner funnel filtration and washed with water (2 mL×3) and dried to afford the desired product 4 with 90% yield.

$^1$H NMR (500 MHz, $CDCl_3$) δ 8.61 (s, 1H), 8.46 (d, J=4.6 Hz, 1H), 8.42 (s, 1H), 8.17 (d, J=7.9 Hz, 1H), 7.81 (s, 1H), 7.75 (s, 2H), 7.32 (dd, J=7.9, 4.6 Hz, 1H), 5.69 (s, 2H), 1.58 (s, 9H). $^{13}$C NMR (126 MHz, $CDCl_3$) δ 162.1, 147.5, 145.6, 144.0, 138.6, 132.4 (q, Jc-f=32.8 Hz), 132.36, 127.8, 127.6, 123.6 (q, Jc-f=274.0 Hz), 122.4, 120.3, 118.8, 117.7, 109.3, 98.5, 83.2, 48.2, 28.1.

(E)-3-(1-(3,5-Bis(trifluoromethyl)benzyl)-1H-pyrrolo[2,3-b]pyridin-3-yl)-2-cyanoacrylic acid (JXL069)

To a solution of 4 (0.5 mmol, 247.5 mg) in dichloromethane (10 mL) was added trifluoroacetic acid (5 equiv, 2.5 mmol, 191 μL). The reaction mixture was stirred at 21° C. for 30 min and a yellow solid precipitated. After the reaction was complete as shown by TLC, the reaction solvent was evaporated by flowing air over the open flask. The solid was washed with 2 mL of the solvent mixture of 5:1 hexanes/EtOAc 5 to 10 times and monitored by TLC until all the non-polar impurities had disappeared. Finally, the purity of the product was checked by NMR. The product (208.5 mg) was isolated in 95% yield.

$^1$H NMR (500 MHz, DMSO-$d_6$) δ 8.85 (s, 1H), 8.47 (m, 2H), 8.43 (m, 1H), 8.09 (s, 2H), 8.04 (s, 1H), 7.35 (dd, J=7.1, 4.6 Hz, 1H), 5.84 (s, 2H). $^{13}$C NMR (126 MHz, DMSO-$d_6$) δ 164.6, 147.8, 146.1, 145.5, 140.6, 135.2, 131.0 (q, Jc-f=32.8 Hz), 129.4, 129.2, 123.6 (q, Jc-f=274.0 Hz), 122.3, 120.1, 119.1, 118.2, 108.7, 97.1, 47.8.

Incorporation by Reference

All publications and patents mentioned herein are hereby incorporated by reference in their entirety as if each individual publication or patent was specifically and individually indicated to be incorporated by reference. In case of conflict, the present application, including any definitions herein, will control.

Equivalents

While specific embodiments of the subject invention have been discussed, the above specification is illustrative and not restrictive. Many variations of the invention will become apparent to those skilled in the art upon review of this specification and the claims below. The full scope of the invention should be determined by reference to the claims, along with their full scope of equivalents, and the specification, along with such variations.

What is claimed is:
1. A method for the preparation of a compound having the following structure:
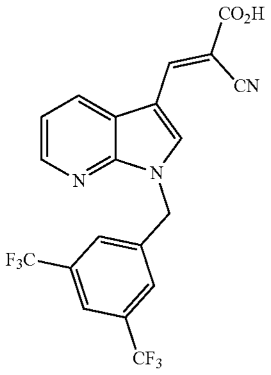
JXL069
or a pharmaceutically acceptable salt thereof;
said method comprising:
reacting
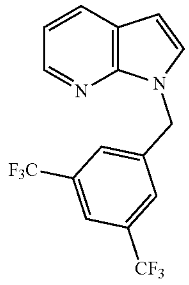 [SMILES: FC(F)(F)c1cc(Cn2ccc3cccnc32)cc(C(F)(F)F)c1]
with an acylation reagent to produce
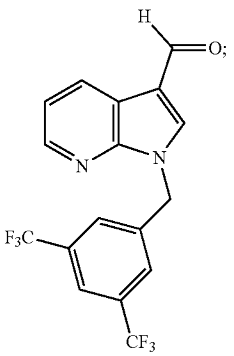 [SMILES: O=Cc1cn(Cc2cc(C(F)(F)F)cc(C(F)(F)F)c2)c2ncccc12]
reacting
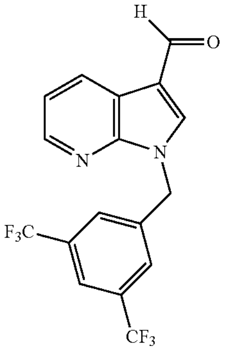 [SMILES: O=Cc1cn(Cc2cc(C(F)(F)F)cc(C(F)(F)F)c2)c2ncccc12]
with
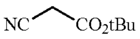
to produce
4
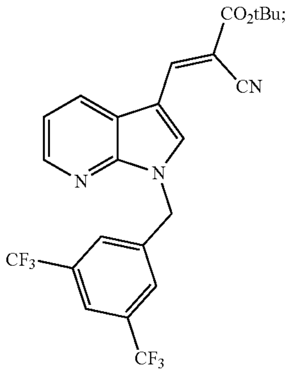
and
further hydrolyzing
4
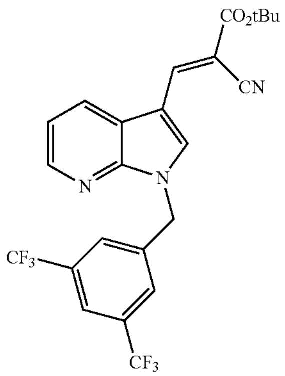

to produce
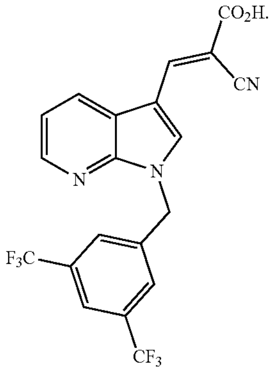
JXL069
2. The method of claim 1, further comprising reacting
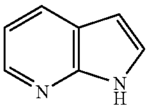
with
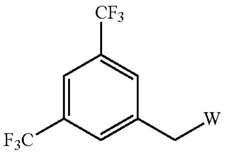
to produce
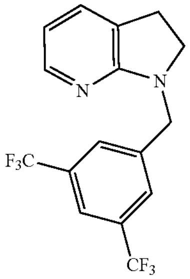
wherein W is a leaving group.
3. The method of claim 2, wherein W is halo.
4. The method of claim 2, wherein W is bromo.
5. The method of claim 1, wherein hydrolyzing compound 4 produces JXL069 in more than 90% yield.
6. The method of claim 1, wherein hydrolyzing compound 4 produces JXL069 in 95% yield.
* * * * *